(12) United States Patent
Alden et al.

(10) Patent No.: US 11,065,095 B2
(45) Date of Patent: Jul. 20, 2021

(54) SAMPLE CONTAINER WITH PEELABLE SEAL AND ACCESS PORT

(71) Applicant: Instant Systems, Inc., Norfolk, VA (US)

(72) Inventors: Madeline C. Alden, Norfolk, VA (US); Kimber L. Burley, Fulton, MD (US); Tara C. Ramsey, Norfolk, VA (US)

(73) Assignee: Instant Systems, Inc., Norfolk, VA (US)

( * ) Notice: Subject to any disclaimer, the term of this patent is extended or adjusted under 35 U.S.C. 154(b) by 199 days.

(21) Appl. No.: 16/460,920

(22) Filed: Jul. 2, 2019

(65) Prior Publication Data

US 2020/0008921 A1     Jan. 9, 2020

Related U.S. Application Data

(60) Provisional application No. 62/694,662, filed on Jul. 6, 2018.

(51) Int. Cl.
*A61F 2/00*     (2006.01)
*B65D 75/58*     (2006.01)
(Continued)

(52) U.S. Cl.
CPC .......... *A61F 2/0095* (2013.01); *A01N 1/0273* (2013.01); *B65B 5/04* (2013.01);
(Continued)

(58) Field of Classification Search
CPC ....... A61F 2/0095; A01N 1/0273; B65B 5/04; B65B 51/10; B65D 65/42; B65D 75/5855
(Continued)

(56) References Cited

U.S. PATENT DOCUMENTS 2,864,492 A    12/1958   Lappala
3,326,450 A     6/1967   Langdon
(Continued)

FOREIGN PATENT DOCUMENTS

CN     202313465 U     7/2012
EP       1 031 341      11/2003
(Continued)

OTHER PUBLICATIONS

BioMet Spine—Cellentra Advanced Allograft, 2015.
(Continued)

*Primary Examiner* — Jacob K Ackun
(74) *Attorney, Agent, or Firm* — ReavesColey PLLC

(57) ABSTRACT

An apparatus includes a flexible container, a port, and a support structure. The container includes a first layer coupled to a second layer to define a storage volume within which a tissue specimen can be contained. The first layer is characterized by a first stiffness and the second layer characterized by a second stiffness. An edge of the first layer is spaced apart from an edge of the second layer to define an opening into the storage volume. The edge of the first layer and the edge of the second layer are configured to form a peelable seal that hermetically seals the storage volume such that the first layer can be peeled away from the second layer to expose the storage volume. The port is coupled to the flexible container and allows fluid communication between the storage volume and an external volume. The support structure is configured to support the tissue specimen within the storage volume and is characterized by a third stiffness. The third stiffness is greater than the first stiffness and the second stiffness.

20 Claims, 12 Drawing Sheets

(51) Int. Cl.
  *A01N 1/02* (2006.01)
  *B65B 5/04* (2006.01)
  *B65B 51/10* (2006.01)
  *B65D 65/42* (2006.01)

(52) U.S. Cl.
  CPC .............. *B65B 51/10* (2013.01); *B65D 65/42* (2013.01); *B65D 75/5855* (2013.01)

(58) Field of Classification Search
  USPC .............................. 206/438, 484, 484.2, 569
  See application file for complete search history.

(56) References Cited

U.S. PATENT DOCUMENTS

| | | | |
|---|---|---|---|
| 3,339,826 A | 9/1967 | Beskind |
| 3,754,700 A | 8/1973 | Bonk |
| 4,035,304 A | 7/1977 | Watanabe |
| 4,152,184 A | 5/1979 | Bacehowski |
| 4,176,746 A | 12/1979 | Kooi |
| 4,561,110 A | 12/1985 | Herbert |
| 4,630,448 A | 12/1986 | Bilstad et al. |
| 4,714,595 A | 12/1987 | Anthony et al. |
| 4,998,671 A | 3/1991 | Leifheit |
| 5,031,762 A | 7/1991 | Heacox |
| 5,088,994 A | 2/1992 | Porat et al. |
| 5,114,004 A | 5/1992 | Isono et al. |
| 5,160,329 A | 11/1992 | Oxley |
| 5,209,745 A | 5/1993 | Irr et al. |
| D337,382 S | 7/1993 | Wallace |
| 5,236,088 A | 8/1993 | Dhority et al. |
| 5,253,754 A | 10/1993 | Soodak |
| 5,360,413 A | 11/1994 | Leason et al. |
| 5,728,086 A | 3/1998 | Niedospial |
| RE36,132 E | 3/1999 | Heacox |
| 6,022,344 A | 2/2000 | Meijer et al. |
| 6,045,546 A | 4/2000 | Drago et al. |
| 6,089,541 A | 7/2000 | Weinheimer et al. |
| 6,176,371 B1 | 1/2001 | Tyrrell |
| 6,287,284 B1 | 9/2001 | Warburton-Pitt |
| 6,367,634 B1 | 4/2002 | Lynn et al. |
| 6,398,771 B1 | 6/2002 | Gustafsson et al. |
| 6,523,698 B1 | 2/2003 | Dennehey et al. |
| 6,648,133 B1 | 11/2003 | Blaschke et al. |
| 6,730,071 B1 | 5/2004 | Dassa |
| 6,773,425 B1 | 8/2004 | Tamari |
| 7,354,426 B2 | 4/2008 | Young |
| D595,842 S | 7/2009 | Haga et al. |
| 7,594,578 B2 | 9/2009 | Smith et al. |
| 7,670,384 B2 | 3/2010 | Kumar et al. |
| 7,770,611 B2 | 8/2010 | Houwaert et al. |
| 7,875,015 B2 | 1/2011 | Pahlberg et al. |
| 8,138,330 B2 | 3/2012 | Ostler et al. |
| 8,267,912 B2 | 9/2012 | Ferris |
| 8,287,680 B2 | 10/2012 | Foucaut et al. |
| 8,597,223 B2 | 12/2013 | D'Ayot et al. |
| D705,443 S | 5/2014 | Ichimura et al. |
| 9,095,499 B2 | 8/2015 | Kugelmann et al. |
| 9,155,606 B2 | 10/2015 | Benoit et al. |
| 9,198,830 B2 | 12/2015 | Kugelmann et al. |
| 9,796,166 B2 | 10/2017 | Verri et al. |
| 9,926,524 B2 | 3/2018 | Clark et al. |
| 9,974,528 B2 | 5/2018 | Taylor et al. |
| 10,582,994 B2 * | 3/2020 | Kapec ................... A61F 2/0095 |
| 2002/0130093 A1 | 9/2002 | Ferrara, Jr. et al. |
| 2004/0161167 A1 | 8/2004 | Ausnit et al. |
| 2005/0271307 A1 | 12/2005 | Pawloski et al. |
| 2006/0024818 A1 | 2/2006 | Conconi |
| 2007/0074980 A1 * | 4/2007 | Bankoski ............. B65D 25/082 |
| | | | 206/219 |
| 2007/0092398 A1 | 4/2007 | McDonald |
| 2008/0214998 A1 | 9/2008 | Kurek et al. |
| 2008/0234654 A1 | 9/2008 | McCarthy et al. |
| 2008/0254471 A1 | 10/2008 | Bordano |
| 2009/0030396 A1 | 1/2009 | Ferris |
| 2009/0105684 A1 | 4/2009 | Balteau et al. |
| 2009/0238495 A1 | 9/2009 | Anderson |
| 2011/0308977 A1 | 12/2011 | DiLiberto et al. |
| 2013/0209000 A1 | 8/2013 | Owensby et al. |
| 2016/0000062 A1 | 1/2016 | Chen et al. |
| 2016/0228231 A1 * | 8/2016 | Southard ............... A61F 2/0095 |
| 2016/0305577 A1 | 10/2016 | Huschke |
| 2017/0001782 A1 | 1/2017 | Arent et al. |
| 2017/0121061 A1 | 5/2017 | Sprehe et al. |
| 2017/0172847 A1 | 6/2017 | Platenkamp et al. |
| 2018/0154289 A1 | 6/2018 | Rhodes |
| 2020/0061365 A1 | 2/2020 | Alden et al. |

FOREIGN PATENT DOCUMENTS

| | | |
|---|---|---|
| WO | WO1997/042897 | 11/1997 |
| WO | WO 2002/041824 | 5/2002 |
| WO | WO 20171026131 | 2/2017 |

OTHER PUBLICATIONS

Clarke, Dominic. "Enabling Fluid Transfer for Cell Therapies: An Industry Challenge," *Pharmaceutical Technology* 41 (4), 2017.
MTF Allograft Tissue—Instructions for Use, Aug. 2011. 2 pages.
International Search Report & Written Opinion mailed in PCT Application No. PCT/US2019/040419 dated Sep. 30, 2019.

* cited by examiner

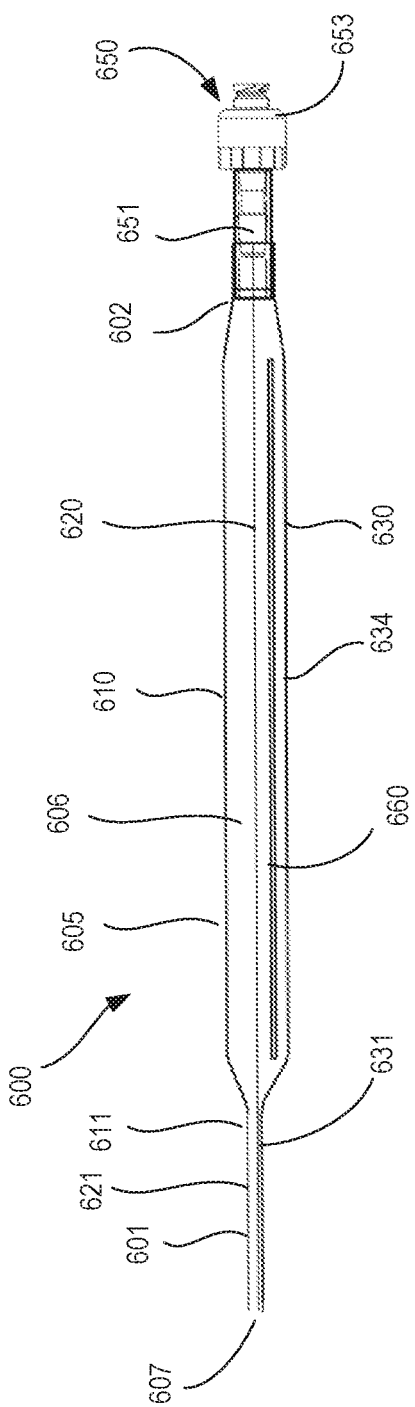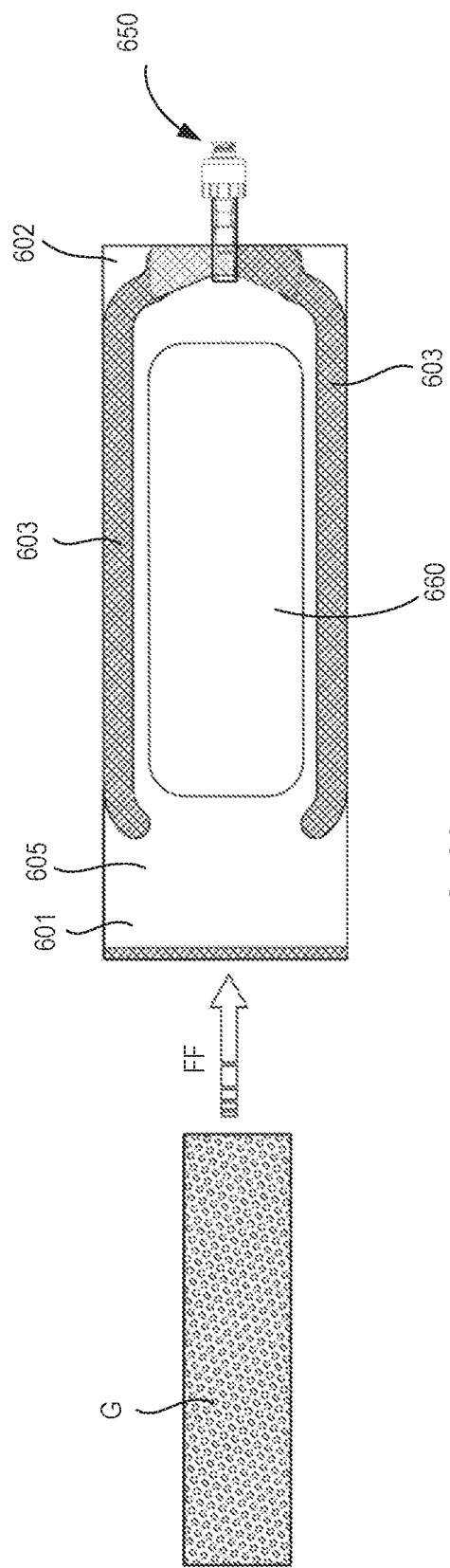

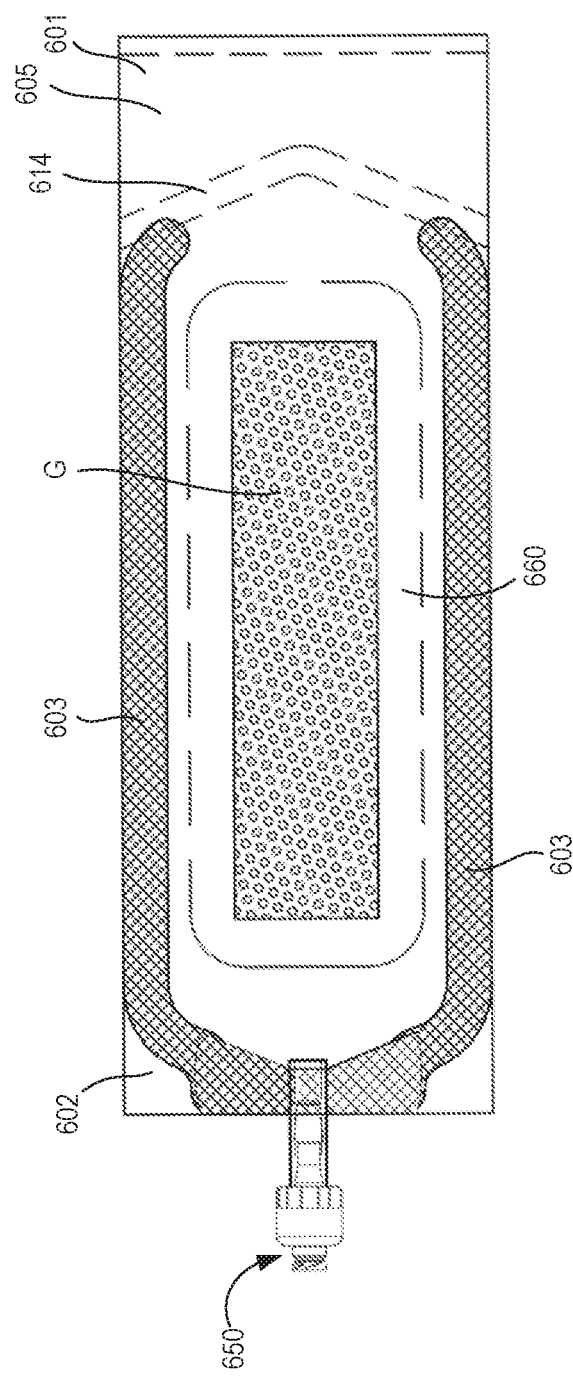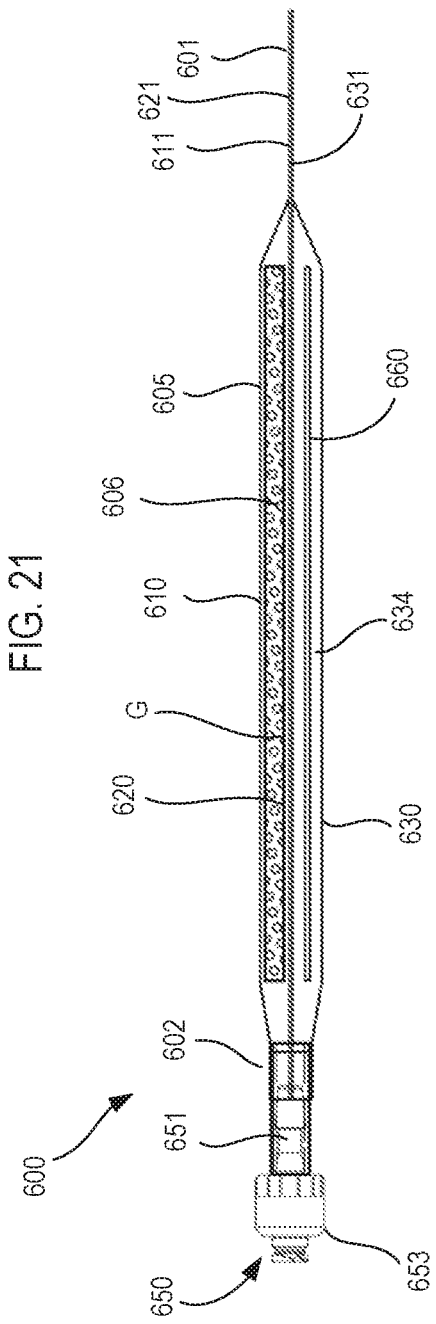
FIG. 21
FIG. 22

SAMPLE CONTAINER WITH PEELABLE SEAL AND ACCESS PORT

CROSS-REFERENCE TO RELATED APPLICATIONS

This application claims priority to U.S. Provisional Application Ser. No. 62/694,662, entitled "Sample Container with Peelable Seal and Access Port," filed Jul. 6, 2018, which is incorporated herein by reference in its entirety.

BACKGROUND

The embodiments described herein relate containers for storing and transporting tissue and other biological material. More particularly, the embodiments described herein relate to devices and methods including containers having a peelable seal and an access port for use in tissue implant procedures.

Known tissue implants and/or grafts are used in a variety of procedures to repair or replace damaged tissue. Such procedures can include implanting bone or gum tissue to address dental or periodontal issues, bone grafting to repair fractures, and tendon grafting to repair damaged ligaments and/or tendons (e.g., repair of a torn anterior cruciate ligament), to name just a few. In many instances, the tissue implant is not taken from the patient's body (i.e., is not an autograft), but rather is from another source, such as from a human cadaver (i.e., an allograft) or an animal (i.e., a xenograft). Known non-autologous grafts are often stored in a dried condition within a sterile package, and thus must be rehydrated or otherwise prepared prior to use.

Some known procedures for preparing or rehydrating a tissue implant include removing the tissue implant from the sterile package and placing the tissue graft in an opened container (e.g., a basin) that contains rehydration liquid. The tissue implant is then manipulated within the open container to facilitate rehydration. Such manipulation can include, for example, manually submerging the tissue implant within the rehydration fluid (in an effort to achieve consistent rehydration), agitating the tissue implant and/or rehydration fluid, and the like. After rehydration, the tissue implant is then removed from the rehydration container for use. This procedure can result in compromised sterility (e.g., due to the repeated transfer of the tissue graft), inconsistent rehydration due to inconsistent exposure of the tissue implant in the open container, and longer rehydration times. Additionally, because of the repeated movement of the tissue implant (e.g., during transfer and while in the rehydration container) possible damage to the tissue implant can occur.

Other known procedures include receiving the tissue implant in a rigid tray, removing a lid from the tray, and completing the rehydration procedure in the open tray. Although this method eliminates the step of transferring the tissue implant from its sterile packaging, such rigid packaging can be bulky and less desirable for tissue storage facilities. Moreover, the rehydration still occurs in an open top container and can involve agitating, submerging, or moving the tissue implant, which can result in damage to the tissue implant.

Yet other known procedures including rehydrating the tissue implant with a sterile, flexible pouch. Such systems and methods often provide inadequate support for the tissue implant, and thus the implant can be easily damaged during the rehydration operation.

Thus, a need exists for improved containers and methods for storing, transporting, and rehydrating tissue and other biological material.

SUMMARY

Containers and methods for storing tissue and other biological materials are described herein. In some embodiments, an apparatus includes a flexible container, a port, and a support structure. The container includes a first layer coupled to a second layer to define a storage volume within which a tissue specimen can be contained. The first layer is characterized by a first stiffness and the second layer characterized by a second stiffness. An edge of the first layer is spaced apart from an edge of the second layer to define an opening into the storage volume. The edge of the first layer and the edge of the second layer are configured to form a peelable seal that hermetically seals the storage volume such that the first layer can be peeled away from the second layer to expose the storage volume. The port is coupled to the flexible container and allows fluid communication between the storage volume and an external volume. The support structure is configured to support the tissue specimen within the storage volume and is characterized by a third stiffness. The third stiffness is greater than the first stiffness and the second stiffness.

In some embodiments, a method includes inserting a tissue specimen into a storage volume defined between a first layer of a flexible container and a second layer of the flexible container. The tissue specimen is inserted via an opening defined by an edge of the first layer and an edge of the second layer. The flexible container includes a port configured to allow fluid communication between the storage volume and an external volume. The tissue specimen is positioned within the storage volume between the first layer and a support structure. A stiffness of the support structure is greater than each of a stiffness of the first layer and a stiffness of the second layer. The edge of the first layer is then coupled to the edge of the second layer to form a peelable seal that hermetically seals the storage volume. The peelable seal is configured such that the first layer can be peeled away from the second layer to expose the storage volume.

BRIEF DESCRIPTION OF THE DRAWINGS

FIG. 19 is a side view and FIG. 20 is a top view of a container assembly in an opened configuration, according to an embodiment.

FIG. 21 is a side view and FIG. 22 is a top view of the container assembly shown in FIGS. 19 and 20 in a sealed configuration with a tissue specimen contained therein.

DETAILED DESCRIPTION

Figure 1:
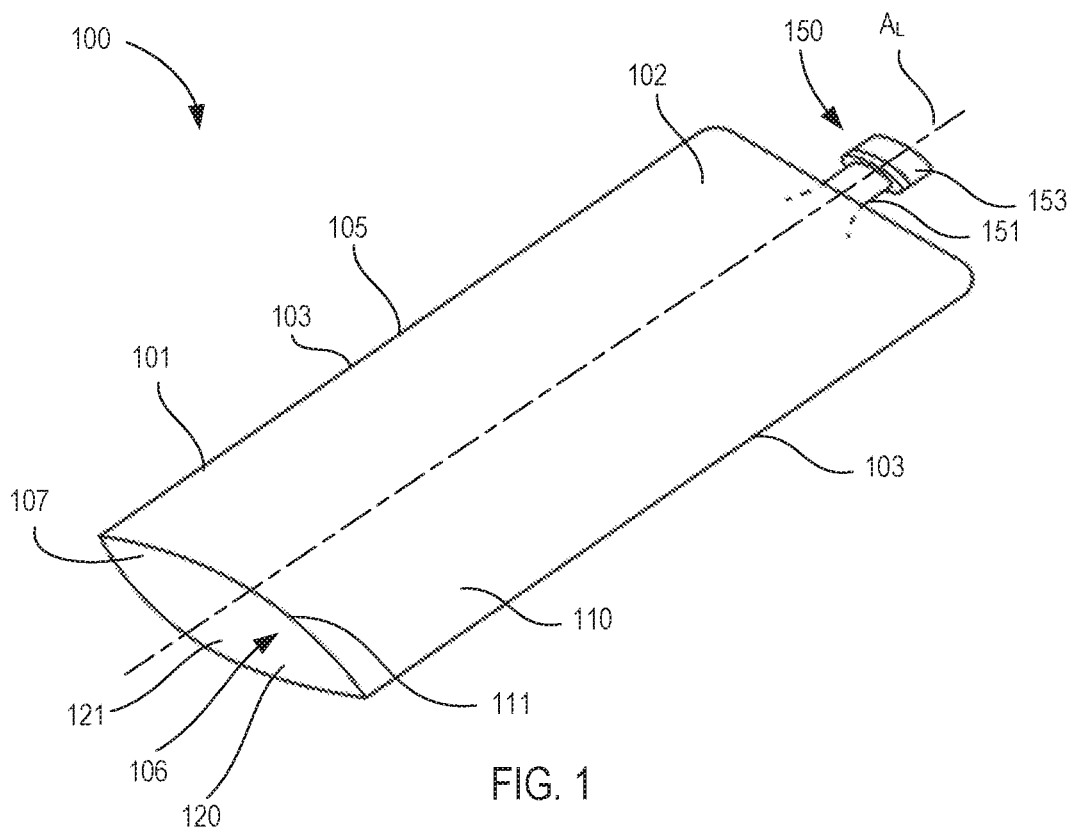
FIGS. 1-4 are schematic illustrations of a container assembly according to an embodiment, in a first configuration (FIG. 1), a second configuration (FIG. 2), a third configuration (FIG. 3), and a fourth configuration (FIG. 4).

The embodiments described herein can advantageously be used in a wide variety of tissue storage, transportation, and implantation operations. In particular, the flexible container designs described herein can allow for a tissue specimen to be loaded and sealed at the point of loading (e.g., a tissue bank) via a peelable seal. The loaded flexible container can be used to both store and rehydrate the tissue specimen within the same container. Moreover, although the container is flexible and easily adaptable for storage, the embodiments described herein include a support member that provides structural support for the tissue specimen during packaging, storage, and rehydration. In this manner, the embodiments described herein can result in more efficient tissue sample storage and rehydration with less damage to the tissue specimen.

In some embodiments, an apparatus includes a flexible container, a port, and a support structure. The container includes a first layer coupled to a second layer to define a storage volume within which a tissue specimen can be contained. The first layer is characterized by a first stiffness and the second layer characterized by a second stiffness. An edge of the first layer is spaced apart from an edge of the second layer to define an opening into the storage volume. The edge of the first layer and the edge of the second layer are configured to form a peelable seal that hermetically seals the storage volume such that the first layer can be peeled away from the second layer to expose the storage volume. The port is coupled to the flexible container and allows fluid communication between the storage volume and an external volume. The support structure is configured to support the tissue specimen within the storage volume and is characterized by a third stiffness. The third stiffness is greater than the first stiffness and the second stiffness.

In some embodiments, an apparatus includes a flexible container, a port, a tissue specimen within the flexible container, and a support structure. The flexible container includes a first layer coupled to a second layer to define a storage volume within which the tissue specimen is contained. The first layer is characterized by a first stiffness and the second layer characterized by a second stiffness. An edge of the first layer is coupled to an edge of the second layer to form a peelable seal that hermetically seals the storage volume such that the first layer can be peeled away from the second layer to expose the storage volume. The port is coupled to the flexible container and allows fluid communication between the storage volume and an external volume. The support structure is coupled to the flexible container and is positioned to support the tissue specimen within the storage volume. The support structure is characterized by a third stiffness that is greater than the first stiffness and the second stiffness.

In some embodiments, an apparatus includes a flexible container, a port, and a support structure. The flexible container includes a first layer, second layer, and a third layer. The first layer is coupled to the second layer to define a storage volume within which a tissue specimen can be contained. The third layer is coupled to the second layer to define a support volume. An edge of the first layer is spaced apart from an edge of the second layer to define an opening into the storage volume, the edge of the first layer and the edge of the second layer configured to form a peelable seal that hermetically seals the storage volume such that the first layer can be peeled away from the second layer to expose the storage volume. The port is coupled to the flexible container and allows fluid communication between the storage volume and the external volume. The support structure is within the support volume and is configured to support the tissue specimen within the storage volume.

In some embodiments, a method includes inserting a tissue specimen into a storage volume defined between a first layer of a flexible container and a second layer of the flexible container. The tissue specimen is inserted via an opening defined by an edge of the first layer and an edge of the second layer. The flexible container includes a port configured to allow fluid communication between the storage volume and an external volume. The tissue specimen is positioned within the storage volume between the first layer and a support structure. A stiffness of the support structure is greater than each of a stiffness of the first layer and a stiffness of the second layer. The edge of the first layer is then coupled to the edge of the second layer to form a peelable seal that hermetically seals the storage volume. The peelable seal is configured such that the first layer can be peeled away from the second layer to expose the storage volume.

In some embodiments, a method of rehydrating a tissue specimen includes conveying a rehydration fluid into a storage volume defined between a first layer of a flexible container and a second layer of the flexible container. The rehydration fluid is conveyed via a port coupled to the flexible container. The storage volume contains a tissue specimen hermetically sealed therein, and the tissue specimen is supported by a support structure. A stiffness of the support structure is greater than each of a stiffness of the first layer and a stiffness of the second layer. The rehydration fluid is maintained within the storage volume to rehydrate the tissue specimen. The first layer is then peeled from the second layer to expose the storage volume. The method further includes removing the rehydrated tissue specimen from the storage volume after the first layer is peeled.

As used herein, the term "about" when used in connection with a referenced numeric indication means the referenced numeric indication plus or minus up to 10% of that referenced numeric indication. For example, the language "about 50" covers the range of 45 to 55. Similarly, the language "about 5" covers the range of 4.5 to 5.5.

As used herein, the term tissue specimen or tissue graft refers to any material that can be used in a tissue repair procedure. Thus, a tissue specimen or a tissue graft can include any of a skin graft, bone tissue, fiber tissue (e.g., tendon tissue, ligament tissue, or the like), ocular tissue (e.g. corneal implants), or the like. A tissue specimen or a tissue graft can include a portion of tissue harvested from a donor or a structure component that includes both tissue and non-tissue material (e.g., a synthetic matrix that includes tissue therein). For example, a tissue specimen or a tissue graft can include bone tissue that also includes bone cement or other non-tissue components. As another example, a tissue specimen or tissue graft can include bone chips including cortical bone chips, cancellous bone chips, and corticocancellous bone chips, and/or bone chips with viable bone lineage committed cells.

As used herein, the term "stiffness" relates to an object's resistance to deflection, deformation, and/or displacement produced by an applied force, and is generally understood to be the opposite of the object's "flexibility." For example, a layer or structure of a container with greater stiffness is more resistant to deflection, deformation and/or displacement when exposed to a force than is a layer or structure of the container having a lower stiffness. Similarly stated, a container (or layer) having a higher stiffness can be characterized as being more rigid than a container (or layer) having a lower stiffness. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of the portion of the object different than the portion of the object to which the force is directly applied. Said another way, in some objects, the point of deflection is distinct from the point where the force is applied.

Stiffness (and therefore, flexibility) is an extensive property of the object being described, and thus is dependent upon the material from which the object is formed as well as certain physical characteristics of the object (e.g., cross-sectional shape, thickness, boundary conditions, etc.). For example, the stiffness of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be decreased, for example, by introducing into the object and/or constructing the object of a material having a relatively low modulus of elasticity. Similarly, the flexural modulus is used to describe the ratio of an applied stress on an object in flexure to the corresponding strain in the outermost portions of the object. The flexural modulus, rather than the modulus of elasticity, is often used to characterize certain materials, for example plastics, that do not have material properties that are substantially linear over a range of conditions. An object with a first flexural modulus is more elastic and has a lower strain on the outermost portions of the object than an object with a second flexural modulus greater than the first flexural modulus. Thus, the stiffness of an object can be reduced by including in the object a material having a relatively low flexural modulus.

Moreover, the stiffness (and therefore flexibility) of an object constructed from a polymer can be influenced, for example, by the chemical constituents and/or arrangement of the monomers within the polymer. For example, the stiffness of an object can be reduced by decreasing a chain length and/or the number of branches within the polymer. The stiffness of an object can also be reduced by including plasticizers within the polymer, which produces gaps between the polymer chains.

The stiffness of an object can also be increased or decreased by changing a physical characteristic of the object, such as the shape or cross-sectional area of the object. For example, an object having a length and a cross-sectional area may have a greater stiffness than an object having an identical length but a smaller cross-sectional area. As another example, the stiffness of an object can be reduced by including one or more stress concentration risers (or discontinuous boundaries) that cause deformation to occur under a lower stress and/or at a particular location of the object. Thus, the stiffness of the object can be decreased by decreasing and/or changing the shape of the object.

As used in this specification, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Figure 2:
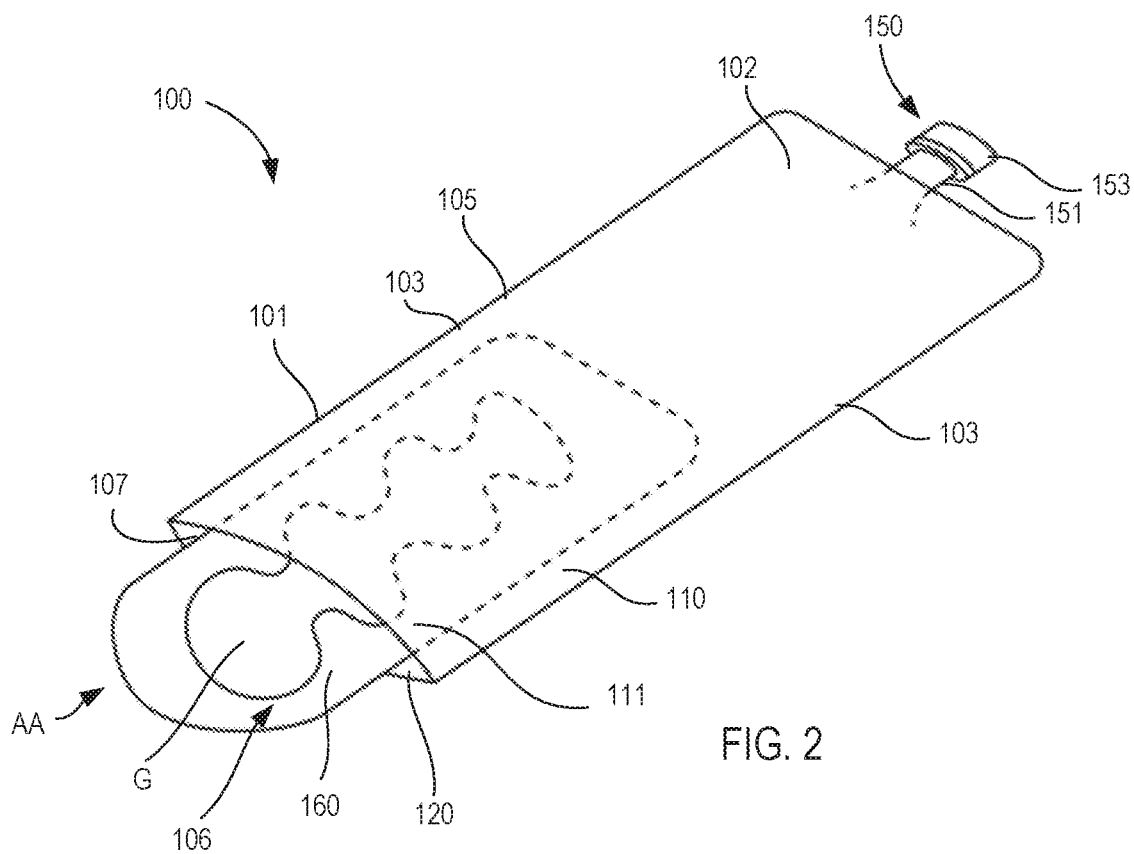
Figure 3:
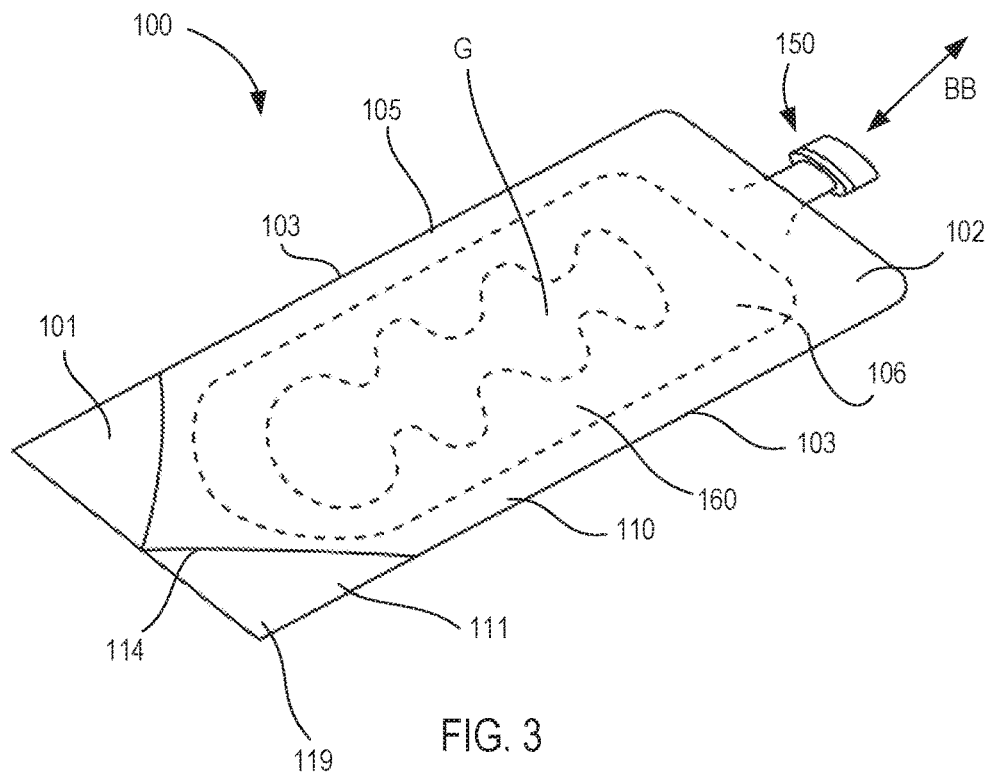
Figure 4:
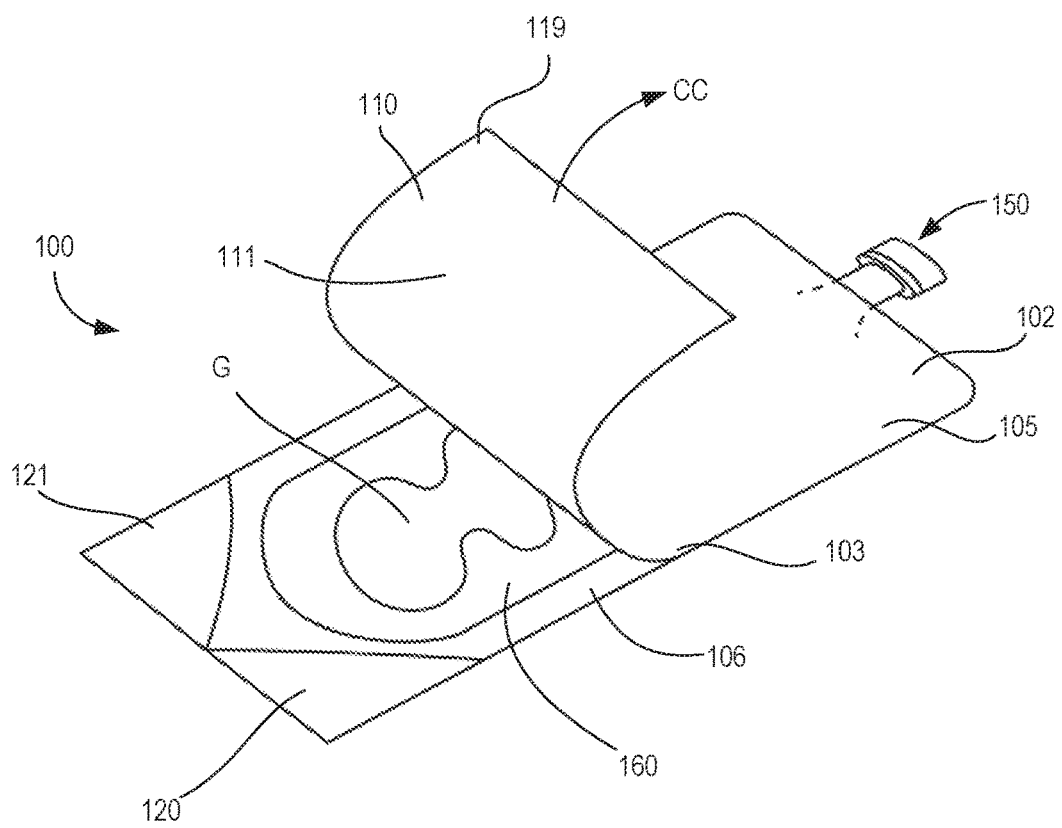

FIGS. 1-4 are schematic illustrations of a container assembly 100 according to an embodiment. The tissue container assembly 100 is shown in a first (or open and unloaded) configuration (FIG. 1), a second (or partially loaded) configuration (FIG. 2), a third (or loaded and sealed) configuration (FIG. 3), and a fourth (opened) configuration (FIG. 4). The container assembly 100 (and any of the container assemblies described herein) can be used to perform any of the methods described herein, such as the method 10 of preparing a tissue specimen for storage (see FIG. 5) and/or the method 20 of rehydrating a tissue specimen for use in a procedure according to an embodiment (see FIG. 6). As described herein, the container assembly 100 provides a single container that can be used for both storage and rehydration. The container provides sufficient support for the tissue specimen or graft G, which can be very fragile during and after rehydration. As shown, the container assembly 100 includes a flexible container 105, a port 150 coupled to the flexible container 105, and a support structure 160.

The flexible container 105 includes a first end portion 101, a second end portion 102, and a pair of side edges 103 between the first end portion 101 and the second end portion 102. The flexible container 105 defines a longitudinal axis AL that extends longitudinally from the first end portion 101 and the second end portion 102. The flexible container 105 is constructed from a first layer 110 and a second layer 120 coupled together to define a storage volume 106. As shown in FIG. 1, when the container assembly 100 is in the first (or opened) configuration, an edge 111 of the first layer 110 is spaced apart from an edge 121 of the second layer 120 to define an opening 107 into the storage volume 106. The opening 107 can be of any suitable size to facilitate loading of the support structure 160 and the tissue specimen G (also referred to as a tissue graft), as described herein. For example, although the opening 107 is shown as extending across the full length of the first end portion 101 of the flexible container 105, in other embodiments, the opening 107 can extend across only a portion of the length of an end or a side of the flexible container 105.

The first layer 110 can be constructed of any suitable material, and has a first stiffness. For example, in some embodiments, the first layer 110 can be a thin, peelable film, such as, for example, a heat seal-coated (HSC) material, a polyethylene material, a polyvinyl chloride (PVC) material, a polyamide material, a polyester-based material, or any combination of such materials, including laminates constructed from multiple different materials. The first layer 110 can have any suitable thickness to provide the desired strength, flexibility, and sealing characteristics. For example, in some embodiments, the first layer 110 can be between about 50 microns (0.050 mm) and about 200 microns (0.200 mm). In other embodiments, the first layer can be between about 50 microns (0.050 mm) and about 100 microns (0.100 mm).

The second layer 120 can be constructed of any suitable material, and has a second stiffness. For example, in some embodiments, the second layer 120 can constructed from the same material and/or can have the same stiffness as the first layer 110. In other embodiments, the second layer 120 can be constructed from a different material and the second stiffness can be different than the first stiffness. The second layer 120 can be constructed from any suitable polymer, such as, for example, a heat seal-coated (HSC) material, a polyethylene material, a polyvinyl chloride (PVC) material, a polyamide material, a polyester-based material, or any combination of such materials, including laminates constructed from multiple different materials. The second layer 120 can have any suitable thickness to provide the desired strength, flexibility, and sealing characteristics. For example, in some embodiments, the second layer 120 can be between about 50 microns (0.050 mm) and about 200 microns (0.200 mm). In other embodiments, the second layer 120 can be between about 50 microns (0.050 mm) and about 100 microns (0.100 mm).

The materials from which the first layer 110 and the second layer 120 are constructed are selected to ensure that the two layers can be joined to hermetically seal the storage volume 106 within which the tissue graft G is stored while also retaining the desired flexibility. Specifically, as shown, the two layers are joined at the second end portion 102 with the port 150 therebetween, and the two side edges 103 are joined together. The two layers can be joined together at the second end portion 102 and along the side edges 103 by any suitable mechanism, such as, for example, by heat bonding or by an adhesive. As shown in FIG. 3, the edge 111 of the first layer 110 and the edge 121 of the second layer 120 are configured to be joined together after the tissue graft G is loaded into the storage volume 106 to form a peelable seal 114 that hermetically seals the storage volume 106. The peelable seal 114 can be configured to have any suitable failure (or peel) mechanism, and can be of any suitable peel strength. For example, in some embodiments, the peelable seal 114 can be an adhesive-based seal in which an adhesive layer pulls back from one of the first layer 110 or the second layer 120 when the first layer 110 is peeled apart from the second layer 120. In other embodiments, the peelable seal 114 can be a cohesive seal in which an adhesive layer or intermediate layer fails within itself when the first layer 110 is peeled apart from the second layer 120. The peelable seal 114 can be produced by any suitable mechanism as described herein, such as, for example, by a heat sealing operation.

By including the peelable seal 114, the container assembly 100 reduces or eliminates the production of particulate matter or other debris that may result from cutting or tearing the flexible container 105 to extract the tissue specimen G. Moreover, the peelable seal 114 can facilitate opening the container assembly 100 in a predetermined fashion and/or in a predetermined direction (e.g., from the first end portion 101 towards the second end portion 102). The inclusion of the peelable seal 114 also eliminates the need for extra tools for opening the container assembly 100 during use.

The peelable seal 114 can be of any suitable geometry to facilitate the desired peel direction, peel strength, and the like. For example, in some embodiments, the peelable seal 114 can be an angled seal that provides for peel tabs 119 that can be grasped by the user to peel the first layer 110 from the second layer. Similarly stated, in some embodiments, the peelable seal 114 can be a chevron seal having any suitable angle.

As described above, the port 150 is coupled to the second end portion 102 of the container assembly 100 and is configured to allow fluid communication (as shown by the arrow BB in FIG. 3) between a volume outside of the container assembly 100 and the storage volume 106. Thus, the port 150 can be used to provide access to the storage volume 106 and the tissue specimen G after the first end portion 101 has been sealed closed. In this manner, the tissue specimen G can be treated with a preservation fluid or other material after being sealed into the container assembly 100. The port 150 can also be coupled to a vacuum source to evacuate the storage volume for storage of the tissue specimen G. Moreover, during a surgical procedure, the port 150 can allow for inflow of rehydration fluid.

The port 150 can be any suitable port that selectively provides fluid communication to the storage volume 106. For example, the port 150 can include a tube 151, a valve, and/or a cap 153. In some embodiments, the port 150 can be a needle-free port. In some embodiments, the port 150 can be a swabable connector. Similarly stated in some embodiments, the port 150 can have external surfaces and can be devoid of recesses or crevices such that the port 150 can be easily wiped or "swabbed" to maintain sterility during use.

In some embodiments, the port 150 can include any of the barbed, swabable valves produced by the Halkey-Roberts Corporation, such as the 2455 series of swabable valves.

Although the port 150 is shown as being coupled at the second end portion 102 of the flexible container 105, in other embodiments, the port 150 (and any of the ports described herein) can be coupled at any location and to any portion of the flexible container 105. For example, in some embodiments, the port 150 (and any of the ports described herein) need not be coupled to an end of the container that is opposite from the end of the container that includes the peelable seal. Similarly, although the port 150 is shown as being aligned with the longitudinal axis $A_L$ of the flexible container 105, in other embodiments, the port 150 (and any of the ports described herein) can be offset from a center line of the flexible container. For example, in some embodiments, the port can be located at a corner of the flexible container. Moreover, the in some embodiments, the port 150 (and any of the ports described herein) can be coupled in a central portion of the flexible container.

The support structure 160 is configured to support the tissue specimen within the storage volume 106. In this manner, the flexible container 105 can be sufficiently flexible to allow inflow and outflow of fluids, vacuum packaging, and rehydration, while the support structure 160 can provide the desired support to limit damage to the tissue specimen G during storage, rehydration, and removal for use in a surgical procedure. The support structure 160 can be constructed of any suitable material, and has a third stiffness that is greater than both the first stiffness (of the first layer 110) and the second stiffness (of the second layer 120). In this manner, the support structure 160 functions as a rigid structure (relative to the flexible container 105) that can support the tissue specimen G during loading into the tissue container 105, storage within the tissue container 105, and subsequent rehydration and preparation for use in a surgical procedure. For example, in some embodiments, the third stiffness is at least two times greater than the first stiffness and the second stiffness. In other embodiments, the third stiffness is at least five times greater than the first stiffness and the second stiffness.

The higher stiffness of the support structure 160 can be related to any of the thickness of the support structure 160, the geometry (i.e., the cross-sectional geometry) of the support structure 160, and the material from which the support structure 160 is constructed. In some embodiments, the support structure 160 can be thicker than either the first layer 110 or the second layer 120. Specifically, in some embodiments, the support structure 160 can be at least twice as thick as either the first layer 110 or the second layer 120. In other embodiments, the support structure 160 can be at least three times as thick as either the first layer 110 or the second layer 120. Moreover, the support structure 160 can be constructed from any suitable polymer, such as, for example, a polyethylene terephthalate (PET) material, a polyethylene material, a polyvinyl chloride (PVC) material, a polyamide material, a polyester-based material, or any combination of such materials, including laminates constructed from multiple different materials. In some embodiments, the support structure 160 can be constructed from a different material than that from which the first layer 110 and/or the second layer 120 are constructed.

Although support structure 160 is shown as being a flat (or planar) structure, in other embodiments, the support structure 160 (and any of the support structures described herein) can be a tray-shaped structure that includes side edges. For example, in some embodiments, any of the container assemblies described herein can include the support structure 460 described herein.

Figure 5:
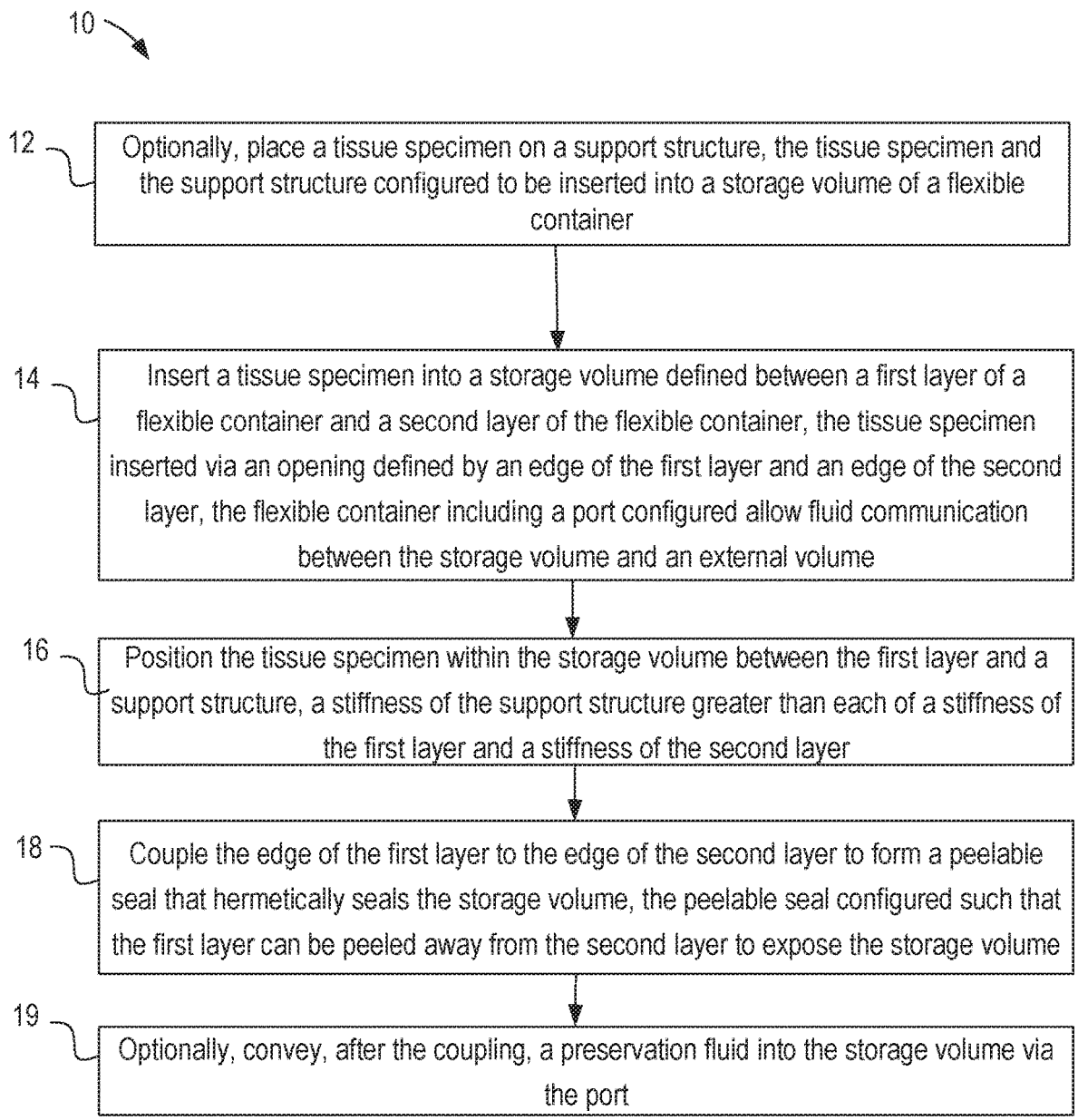
FIG. 5 is a flow diagram of a method of preparing a tissue specimen for storage according to an embodiment.

In some embodiments, the container assembly 100 can be used to store the tissue specimen G for later use. For example, FIG. 5 is a flow chart showing a method 10 of preparing a tissue specimen G for storage according to an embodiment. Although the method 10 is described with reference to the container assembly 100 shown in FIGS. 1-4, the method 10 can be performed with any of the container assemblies described herein. As shown in FIG. 2, the method 10 optionally includes placing the tissue specimen G on the support structure 160, at 12. The tissue specimen G (and in some cases, the tissue specimen G preloaded onto the support structure 160) is then inserted into the storage volume 106 of the flexible container 105, at 14. Specifically, as shown in FIG. 2, the tissue specimen G can be inserted through the opening 107, as shown by the arrow AA. The tissue specimen G can then be positioned within the storage volume 106 between the first layer 110 and the support structure 160, at 16. Said another way, the tissue specimen G can be positioned on top of the support structure 160 and beneath the first layer 110.

After the tissue specimen G is within the storage volume 106, the edge 111 of the first layer 110 is then coupled to the edge 121 of the second layer 120 to form the peelable seal 114, at 18 (see also FIG. 3). As described above, the peelable seal 114 hermetically seals the storage volume 106 and is configured such that the first layer 110 can be peeled away from the second layer 120 to expose the storage volume 106. The peelable seal 114 can be formed by any suitable mechanism. For example, in some embodiments, the peelable seal 114 can be formed by a heat sealer that applies a predetermined pressure and temperature to a portion of the edges 111, 121.

After the tissue specimen G is sealed within the storage volume 106, the port 150 can be used to further prepare the tissue specimen G and/or the entire container assembly 100 for storage. For example, in some embodiment, the method 10 optionally includes conveying a preservation fluid into the storage volume via the port 150, at 19. In other embodiments, the method optionally includes evacuating air and/or other fluids from the storage volume 106 via the port 150. The support structure 160 provides the desired support for the tissue specimen G during the loading, preparation and/or storage process.

Figure 6:
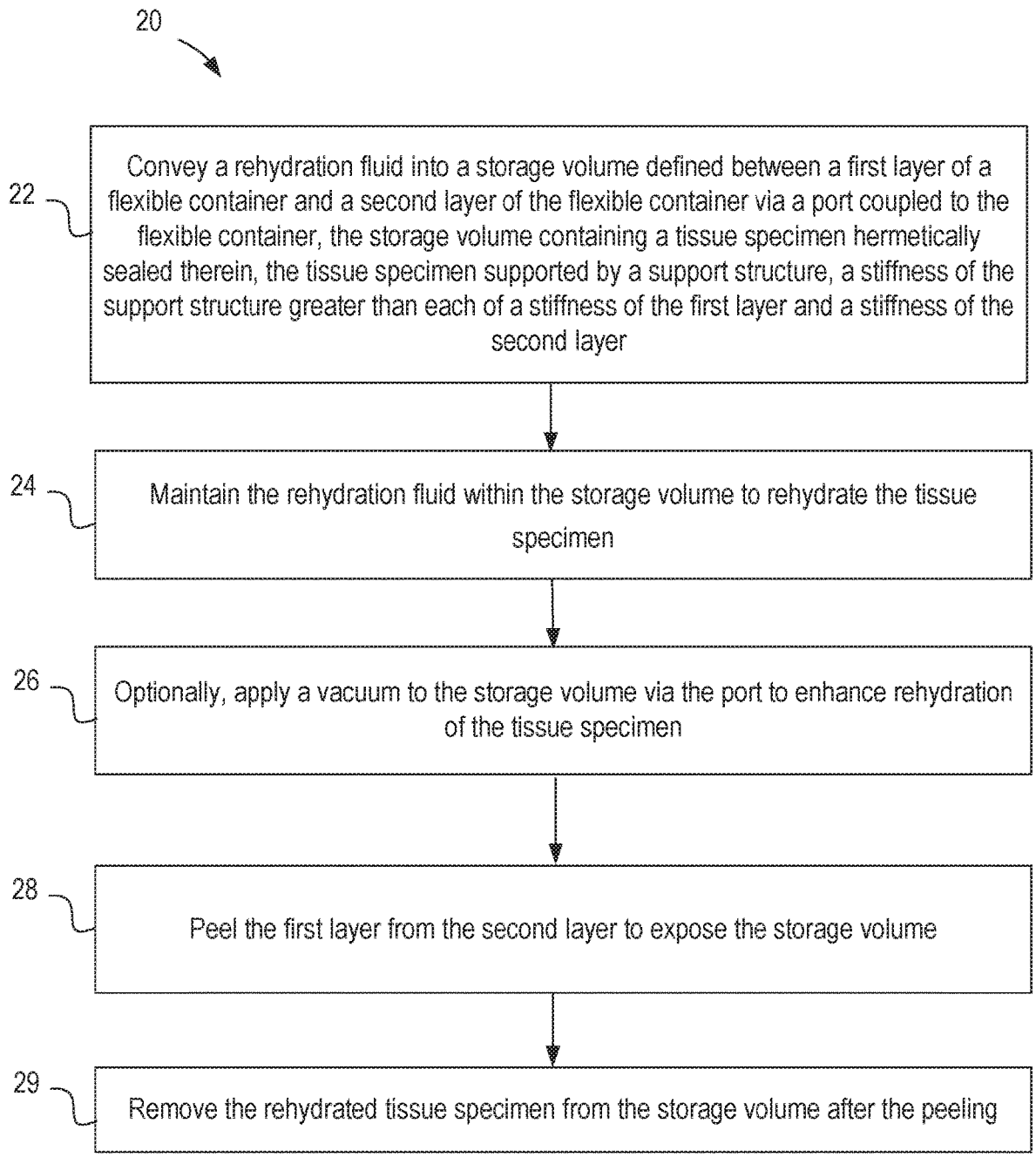
FIG. 6 is a flow diagram of a method of rehydrating a tissue specimen for use in a procedure according to an embodiment.
Figure 7:
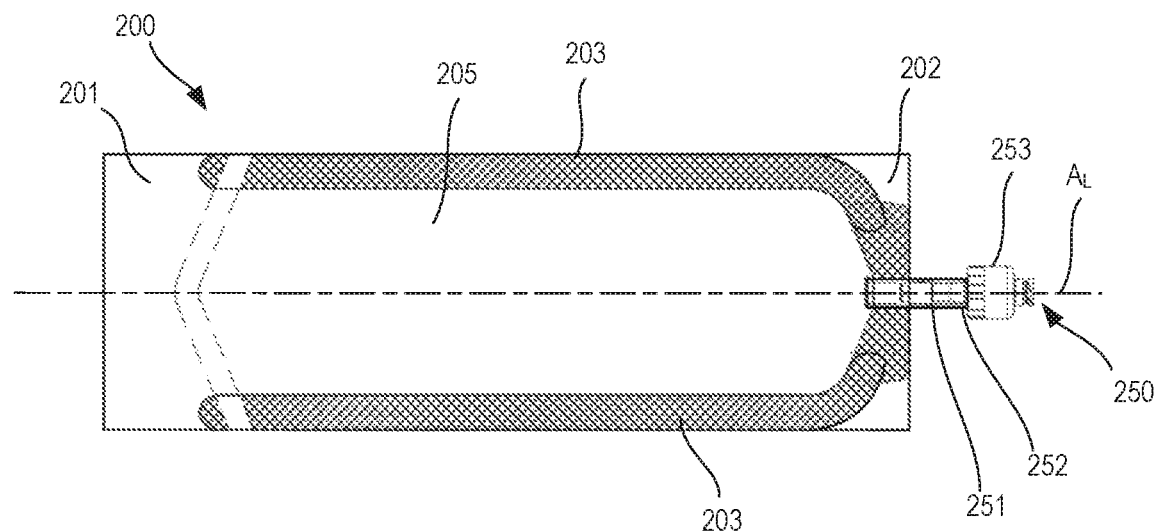
FIG. 7 is a top view and FIG. 8 is a side view of a container assembly in an opened configuration, according to an embodiment.
Figure 8:
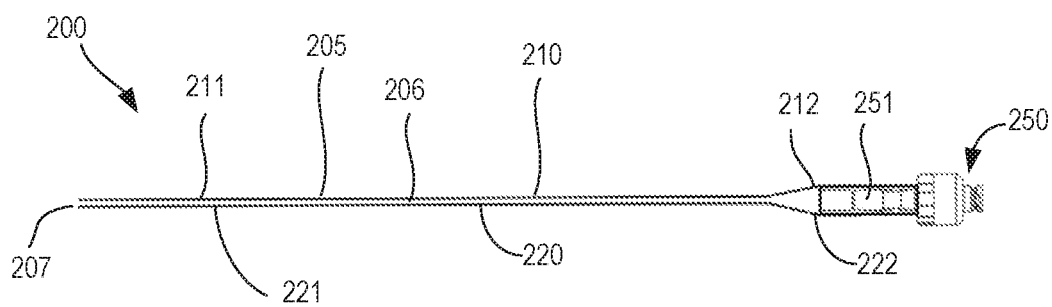
Figure 9:
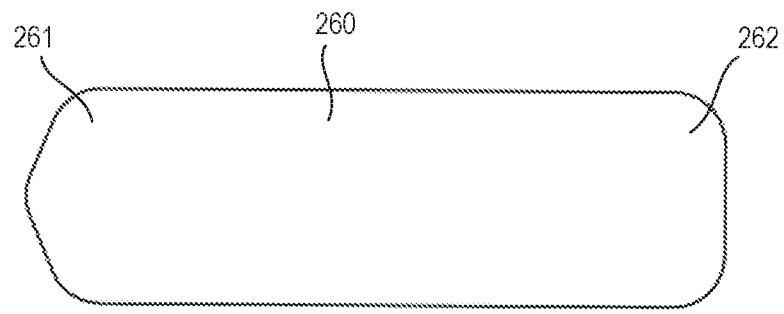
FIG. 9 is a top view of a support structure of the container assembly shown in FIGS. 7 and 8.
Figure 10:
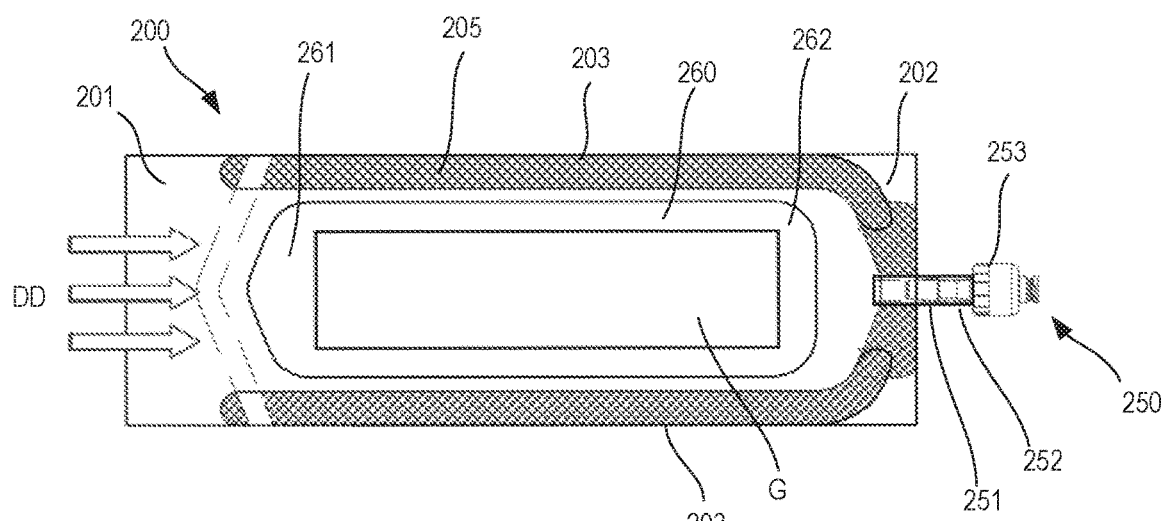
FIG. 10 is a top view of the container assembly shown in FIGS. 7 and 8 with the support structure and a tissue specimen contained therein.

In some embodiments, the container assembly 100 can be used to rehydrate or otherwise prepare the tissue specimen G for use in a procedure. For example, FIG. 6 is a flow chart showing a method 20 of rehydrating a tissue specimen G for use in a procedure, according to an embodiment. Although the method 20 is described with reference to the container assembly 100 shown in FIGS. 1-4, the method 20 can be performed with any of the container assemblies described herein. As shown by the arrow BB in FIG. 3, the method 20 includes conveying a rehydration fluid into the storage volume 106 via the port 150 coupled to the flexible container, at 22. The hydration fluid can be saline solution, blood or any other suitable hydration fluid, and can be conveyed into the storage volume 106 at any suitable pressure.

The rehydration fluid is then maintained within the storage volume 106 to sufficiently rehydrate the tissue graft G, at 24. Because the tissue graft G is sealed within the flexible container, there is no need to manipulate the tissue specimen G to ensure that the tissue specimen remains submerged or fully immersed within the rehydration fluid. Rather, the desired amount of rehydration fluid can be conveyed into the storage volume 106 to ensure that the tissue specimen G is fully immersed. Moreover, the container assembly 100 including the tissue graft G can be rotated (e.g., turned upside down) and gently manipulated to facilitate a thorough and rapid rehydration. During such manipulation, the support structure 160 provides support for the tissue graft G. In some embodiments, the method can include applying a vacuum via the port 150 to perform a vacuum rehydration procedure, at 26.

After the tissue specimen G is sufficiently rehydrated, the first layer 110 is then peeled from the second layer 120 to expose the storage volume 106 (and the tissue specimen G therein), at 28. This is shown in FIG. 4 by the arrow CC. The rehydrated tissue specimen G can then be removed from the storage volume, at 29. In some embodiments, the rehydrated tissue can be removed along with the support structure.

FIGS. 7-11 are various views of a container assembly 200 according to an embodiment. The container assembly 200 (and any of the container assemblies described herein) can be used to perform any of the methods described herein, such as the method 10 of preparing a tissue specimen for storage (see FIG. 5) and/or the method 20 of rehydrating a tissue specimen for use in a procedure according to an embodiment (see FIG. 6). As described herein, the container assembly 200 provides a single container that can be used for both storage and rehydration. The container provides sufficient support for the tissue specimen or graft G, which can be very fragile during and after rehydration. As shown, the container assembly 200 includes a flexible container 205, a port 250 coupled to the flexible container 205, and a support structure 260.

The flexible container 205 includes a first end portion 201, a second end portion 202, and a pair of side edges 203 between the first end portion 201 and the second end portion 202. The flexible container 205 defines a longitudinal axis AL that extends longitudinally from the first end portion 201 and the second end portion 202. The flexible container 205 is constructed from a first layer 210 and a second layer 220 coupled together to define a storage volume 206. As shown in the side view of FIG. 8, when the container assembly 200 is in the first (or opened) configuration, an edge 211 of the first layer 210 is spaced apart from an edge 221 of the second layer 220 to define an opening 207 into the storage volume 206. The opening 207 can be of any suitable size to facilitate loading of the support structure 260 and the tissue specimen G, as described herein. For example, although the opening 207 is shown as extending across the full length of the first end portion 201 of the flexible container 205, in other embodiments, the opening 207 can extend across only a portion of the length of an end or a side of the flexible container 205.

The first layer 210 can be constructed of any suitable material, and has a first stiffness. For example, in some embodiments, the first layer 210 can be a thin, peelable film, such as, for example, a heat seal-coated (HSC) material, a polyethylene material, a polyvinyl chloride (PVC) material, a polyamide material, a polyester-based material, or any combination of such materials, including laminates constructed from multiple different materials. For example, in some embodiments, the first layer 210 is a laminate that includes a substrate, a barrier coating, and an adhesive. The substrate can be, for example, a peelable film of the types (and thicknesses) described herein. The barrier coating can be any suitable coating, such as an aluminum oxide barrier coating of any suitable thickness (36 gauge, 40 gauge, 48 gauge, or any thickness therebetween). The adhesive can be any suitable adhesive that facilitates bonding of the first layer 210 to the second layer 220. Moreover, the first layer 210 can have any suitable thickness to provide the desired strength, flexibility, and sealing characteristics. For example, in some embodiments, the first layer 210 can be between about 50 microns (0.050 mm) and about 200 microns (0.200 mm). In other embodiments, the first layer can be between about 50 microns (0.050 mm) and about 100 microns (0.100 mm).

The second layer 220 can be constructed of any suitable material, and has a second stiffness. For example, in some embodiments, the second layer 220 can constructed from the same material and/or can have the same stiffness as the first layer 210. In other embodiments, the second layer 220 can be constructed from a different material and the second stiffness can be different than the first stiffness. The second layer 220 can be constructed from any suitable polymer, such as, for example, a heat seal-coated (HSC) material, a polyethylene material, a polyvinyl chloride (PVC) material, a polyamide material, a polyester-based material, or any combination of such materials, including laminates constructed from multiple different materials. For example, in some embodiments, the second layer 220 is a laminate that includes a substrate, a barrier coating, and an adhesive. The substrate can be constructed from any of the materials described herein. The barrier coating can be any suitable coating, such as an aluminum oxide barrier coating of any suitable thickness (36 gauge, 40 gauge, 48 gauge, or any thickness therebetween). The adhesive can be any suitable adhesive that facilitates bonding of the first layer 210 to the second layer 220. Moreover, the second layer 220 can have any suitable thickness to provide the desired strength, flexibility, and sealing characteristics. For example, in some embodiments, the second layer 220 can be between about 50 microns (0.050 mm) and about 200 microns (0.200 mm). In other embodiments, the second layer 220 can be between about 50 microns (0.050 mm) and about 100 microns (0.100 mm).

Figure 11:
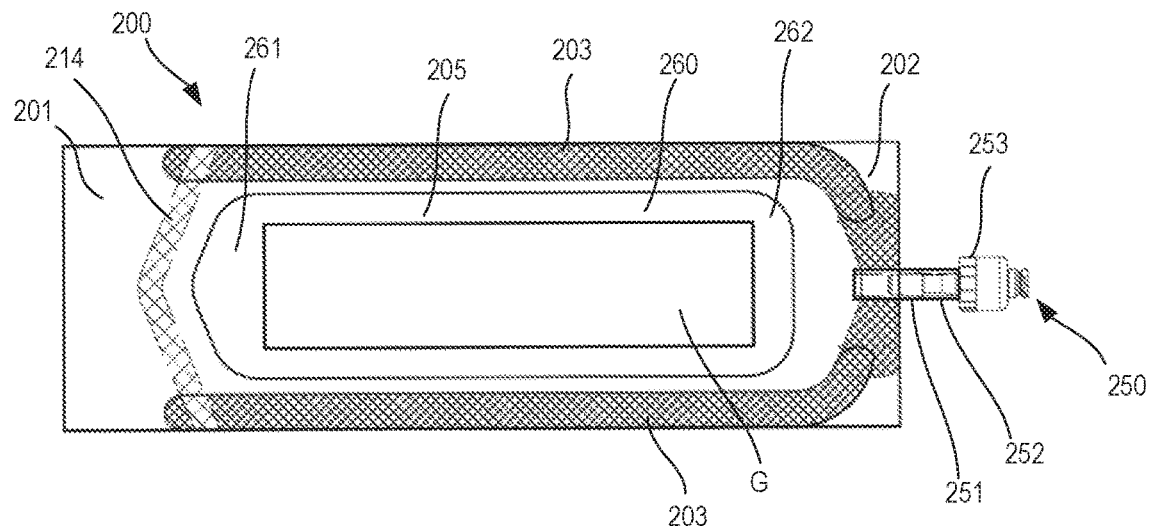
FIG. 11 is a top view of the container assembly shown in FIG. 10 in a sealed configuration.
Figure 12:
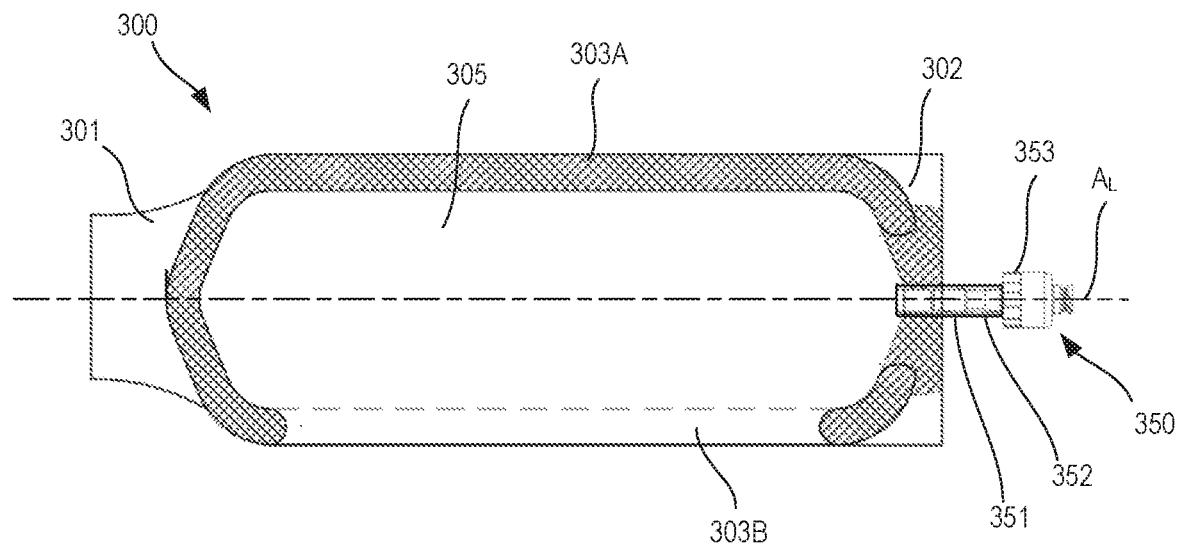
FIG. 12 is a top view and FIG. 13 is a side view of a container assembly in an opened configuration, according to an embodiment.
Figure 13:
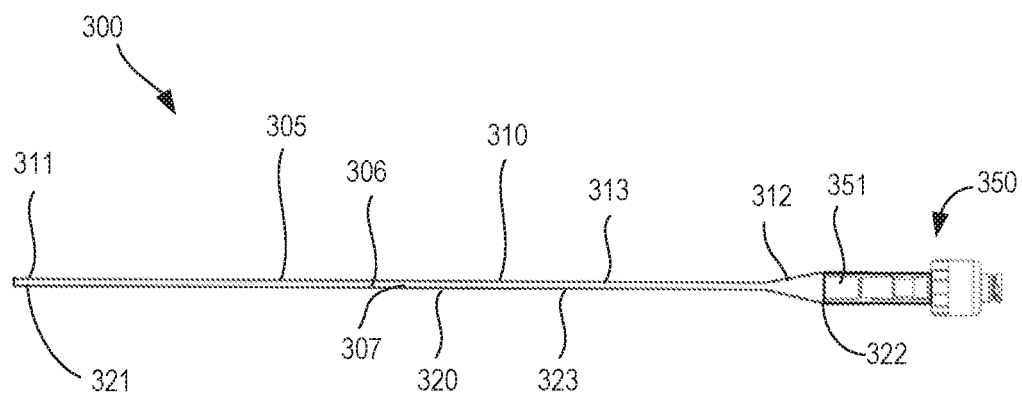
Figure 14:
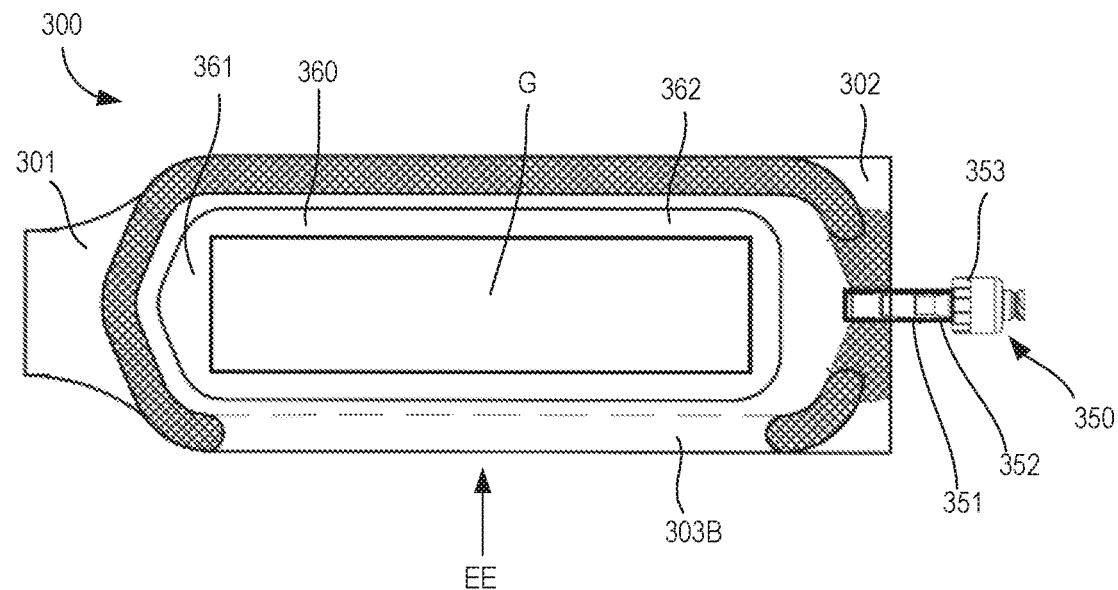
FIG. 14 is a top view of the container assembly shown in FIGS. 12 and 13 with the support structure and a tissue specimen contained therein.

The materials from which the first layer 210 and the second layer 220 are constructed are selected to ensure that the two layers can be joined to hermetically seal the storage volume 206 within which the tissue graft G is stored while also retaining the desired flexibility. Specifically, as shown, the two layers are joined at the second end portion 202 with the port 250 therebetween, and the two side edges 203 are joined together. The two layers can be joined together at the second end portion 202 and along the side edges 203 by any suitable mechanism, such as, for example, by heat bonding or by an adhesive. As shown in FIG. 11, the edge 211 of the first layer 210 and the edge 221 of the second layer 220 are configured to be joined together after the tissue graft G is loaded into the storage volume 206 to form a peelable seal 214 that hermetically seals the storage volume 206. The peelable seal 214 can be configured to have any suitable failure (or peel) mechanism as described herein, and can be of any suitable peel strength. The peelable seal 214 can be produced by any suitable mechanism as described herein, such as, for example, by a heat sealing operation.

By including the peelable seal 214, the container assembly 200 reduces or eliminates the production of particulate matter or other debris that may result from cutting or tearing the flexible container 205 to extract the tissue specimen G. Moreover, the peelable seal 214 can facilitate opening the container assembly 200 in a predetermined fashion and/or in a predetermined direction (e.g., from the first end portion 201 towards the second end portion 202). The inclusion of the peelable seal 214 also eliminates the need for extra tools for opening the container assembly 200 during use.

The peelable seal 214 can be of any suitable geometry to facilitate the desired peel direction, peel strength, and the like. For example, in some embodiments, the peelable seal 214 can be an angled seal that provides for peel tabs that can be grasped by the user to peel the first layer 210 from the second layer. Similarly stated, in some embodiments, the peelable seal 214 can be a chevron seal having any suitable angle.

As described above, the port 250 is coupled to the second end portion 202 of the container assembly 200 and is configured to allow fluid communication between a volume outside of the container assembly 200 and the storage volume 206. Thus, the port 250 can be used to provide access to the storage volume 206 and the tissue specimen G after the first end portion 201 has been sealed closed. In this manner, the tissue specimen G can be treated with a preservation fluid or other material after being sealed into the container assembly 200. The port 250 can also be coupled to a vacuum source to evacuate the storage volume for storage of the tissue specimen G. Moreover, during a surgical procedure, the port 250 can allow for inflow of rehydration fluid.

The port 250 can be any suitable port that selectively provides fluid communication to the storage volume 206. For example, the port 250 can include a tube 251, a valve 252, and/or a cap 253. In some embodiments, the port 250 can be a needle-free port. In some embodiments, the port 250 can be a swabable connector. Similarly stated in some embodiments, the port 250 can have external surfaces and can be devoid of recesses or crevices such that the port 250 can be easily wiped or "swabbed" to maintain sterility during use. In some embodiments, the port 250 can include any of the barbed, swabable valves produced by the Halkey-Roberts Corporation, such as the 2455 series of swabable valves.

The support structure 260 includes a first end 261 and a second end 262, and is configured to support the tissue specimen within the storage volume 206. In this manner, the flexible container 205 can be sufficiently flexible to allow inflow and outflow of fluids, vacuum packaging, and rehydration, while the support structure 260 can provide the desired support to limit damage to the tissue specimen G during storage, rehydration, and removal for use in a surgical procedure. The support structure 260 can be constructed of any suitable material, and has a third stiffness that is greater than both the first stiffness (of the first layer 210) and the second stiffness (of the second layer 220). In this manner, the support structure 260 functions as a rigid structure (relative to the flexible container 205) that can support the tissue specimen G during loading into the tissue container 205, storage within the tissue container 205, and subsequent rehydration and preparation for use in a surgical procedure. For example, in some embodiments, the third stiffness is at least two times greater than the first stiffness and the second stiffness. In other embodiments, the third stiffness is at least five times greater than the first stiffness and the second stiffness.

The higher stiffness of the support structure 260 can be related to any of the thickness of the support structure 260, the geometry (i.e., the cross-sectional geometry) of the support structure 260, and the material from which the support structure 260 is constructed. In some embodiments, the support structure 260 can be thicker than either the first layer 210 or the second layer 220. Specifically, in some embodiments, the support structure 260 can be at least twice as thick as either the first layer 210 or the second layer 220. In other embodiments, the support structure 260 can be at least three times as thick as either the first layer 210 or the second layer 220. Moreover, the support structure 260 can be constructed from any suitable polymer, such as, for example, a polyethylene terephthalate (PET) material, a polyethylene material, a polyvinyl chloride (PVC) material, a polyamide material, a polyester-based material, or any combination of such materials, including laminates constructed from multiple different materials. In some embodiments, the support structure 260 can be constructed from a different material than that from which the first layer 210 and/or the second layer 220 are constructed.

Although support structure 260 is shown as being a flat (or planar) structure, in other embodiments, the support structure 260 (and any of the support structures described herein) can be a tray-shaped structure that includes side edges. For example, in some embodiments, any of the container assemblies described herein can include the support structure 460 described herein.

Although the flexible container 205 is shown as having the opening 207 and the peelable seal 214 being at the first end portion 201 of the container opposite from the second end portion 202 at which the port 250 is located, in other embodiments, the port 250 and the peelable seal (and "loading" opening) can be at any portion of the flexible container. For example, FIGS. 12-15 are various views of a container assembly 300 according to an embodiment that includes a "side opening" configuration. The container assembly 300 (and any of the container assemblies described herein) can be used to perform any of the methods described herein, such as the method 10 of preparing a tissue specimen for storage (see FIG. 5) and/or the method 20 of rehydrating a tissue specimen for use in a procedure according to an embodiment (see FIG. 6). As described herein, the container assembly 300 provides a single container that can be used for both storage and rehydration. The container provides sufficient support for the tissue specimen or graft G, which can be very fragile during and after rehydration. As shown, the container assembly 300 includes a flexible container 305, a port 350 coupled to the flexible container 305, and a support structure 360.

The flexible container 305 includes a first end portion 301, a second end portion 302, and a pair of side edges 303A and 303B between the first end portion 301 and the second end portion 302. The flexible container 305 defines a longitudinal axis $A_L$ that extends longitudinally from the first end portion 301 and the second end portion 302. The flexible container 305 is constructed from a first layer 310 and a second layer 320 coupled together to define a storage volume 306. As shown in the side view of FIG. 13 and in contrast to the flexible container 205, when the container assembly 300 is in the first (or opened) configuration, the end edge 311 of the first layer 310 is coupled to the corresponding end edge 321 of the second layer 320 to seal the first end portion 301 of the container. Instead, a side edge 313 of the first layer 310 is spaced apart from the corresponding side edge 323 of the second layer 320 to define a side opening 307 (along the side edge 303B of the container) into the storage volume 306. The opening 307 can be of any suitable size to facilitate loading of the support structure 360 and the tissue specimen G, as described herein.

The first layer 310 can be constructed of any suitable material, and has a first stiffness. For example, in some embodiments, the first layer 310 can be a thin, peelable film, such as, for example, a heat seal-coated (HSC) material, a polyethylene material, a polyvinyl chloride (PVC) material, a polyamide material, a polyester-based material, or any combination of such materials, including laminates constructed from multiple different materials. For example, in some embodiments, the first layer 310 is a laminate that includes a substrate, a barrier coating, and an adhesive. The substrate can be, for example, a peelable film of the types (and thicknesses) described herein. The barrier coating can be any suitable coating, such as an aluminum oxide barrier coating of any suitable thickness (36 gauge, 40 gauge, 48 gauge, or any thickness therebetween). The adhesive can be any suitable adhesive that facilitates bonding of the first layer 310 to the second layer 320. Moreover, the first layer 310 can have any suitable thickness to provide the desired strength, flexibility, and sealing characteristics. For example, in some embodiments, the first layer 310 can be between about 50 microns (0.050 mm) and about 200 microns (0.200 mm). In other embodiments, the first layer can be between about 50 microns (0.050 mm) and about 100 microns (0.100 mm).

The second layer 320 can be constructed of any suitable material, and has a second stiffness. For example, in some embodiments, the second layer 320 can constructed from the same material and/or can have the same stiffness as the first layer 310. In other embodiments, the second layer 320 can be constructed from a different material and the second stiffness can be different than the first stiffness. The second layer 320 can be constructed from any suitable polymer, such as, for example, a heat seal-coated (HSC) material, a polyethylene material, a polyvinyl chloride (PVC) material, a polyamide material, a polyester-based material, or any combination of such materials, including laminates constructed from multiple different materials. For example, in some embodiments, the second layer 320 is a laminate that includes a substrate, a barrier coating, and an adhesive. The substrate can be constructed from any of the materials described herein. The barrier coating can be any suitable coating, such as an aluminum oxide barrier coating of any suitable thickness (36 gauge, 40 gauge, 48 gauge, or any thickness therebetween). The adhesive can be any suitable adhesive that facilitates bonding of the first layer 310 to the second layer 320. Moreover, the second layer 320 can have any suitable thickness to provide the desired strength, flexibility, and sealing characteristics. For example, in some embodiments, the second layer 320 can be between about 50 microns (0.050 mm) and about 200 microns (0.200 mm). In other embodiments, the second layer 320 can be between about 50 microns (0.050 mm) and about 100 microns (0.100 mm).

Figure 15:
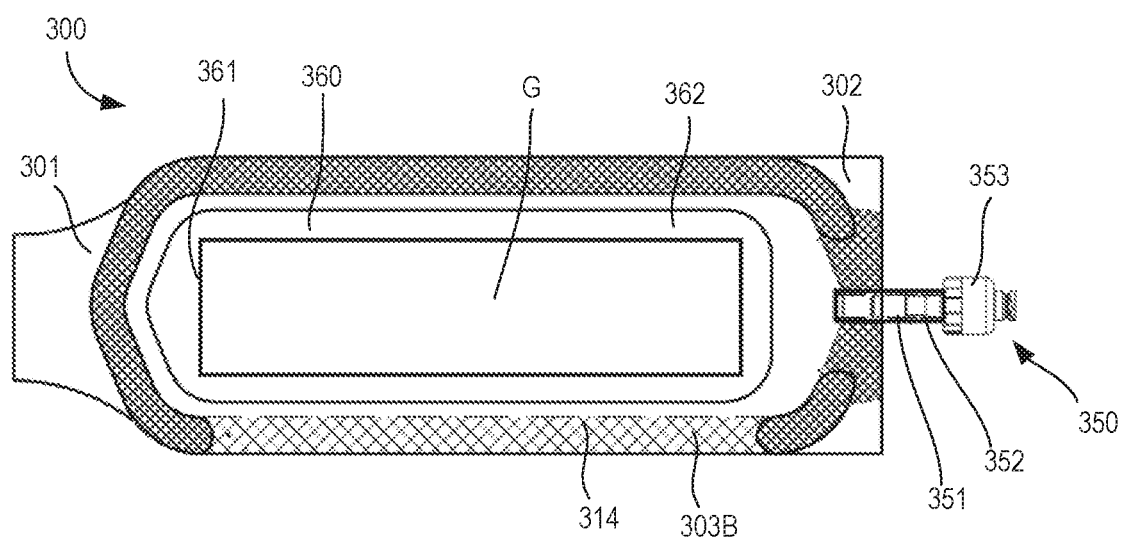
FIG. 15 is a top view of the container assembly shown in FIG. 13 in a sealed configuration.

The materials from which the first layer 310 and the second layer 320 are constructed are selected to ensure that the two layers can be joined to hermetically seal the storage volume 306 within which the tissue graft G is stored while also retaining the desired flexibility. Specifically, as shown, the two layers are joined at the first end portion 301 and at the second end portion 302 with the port 350 therebetween. The first side edge 303A is also joined together, leaving the opening 307 along the second side edge 303B. The two layers can be joined together at the second end portion 302 and along the side edges 303 by any suitable mechanism, such as, for example, by heat bonding or by an adhesive. As shown in FIG. 15, the edge 311 of the first layer 310 and the edge 321 of the second layer 320 are configured to be joined together after the tissue graft G is loaded into the storage volume 306 to form a peelable seal 314 that hermetically seals the storage volume 306. The peelable seal 314 can be configured to have any suitable failure (or peel) mechanism as described herein, and can be of any suitable peel strength.

The peelable seal 314 can be produced by any suitable mechanism as described herein, such as, for example, by a heat sealing operation.

The peelable seal 314 can be of any suitable geometry to facilitate the desired peel direction, peel strength, and the like. For example, in some embodiments, the peelable seal 314 can be an angled seal that provides for peel tabs that can be grasped by the user to peel the first layer 310 from the second layer. Similarly stated, in some embodiments, the peelable seal 314 can be a chevron seal having any suitable angle.

As described above, the port 350 is coupled to the second end portion 302 of the container assembly 300 and is configured to allow fluid communication between a volume outside of the container assembly 300 and the storage volume 306. Thus, the port 350 can be used to provide access to the storage volume 306 and the tissue specimen G after the first end portion 301 has been sealed closed. In this manner, the tissue specimen G can be treated with a preservation fluid or other material after being sealed into the container assembly 300. The port 350 can also be coupled to a vacuum source to evacuate the storage volume for storage of the tissue specimen G. Moreover, during a surgical procedure, the port 350 can allow for inflow of rehydration fluid. The port 350 can be any suitable port that selectively provides fluid communication to the storage volume 306, such as the port 250 described above. The port 350 can include a tube 351, a valve 352, and/or a cap 353.

The support structure 360 includes a first end 361 and a second end 362, and is configured to support the tissue specimen within the storage volume 306. In this manner, the flexible container 305 can be sufficiently flexible to allow inflow and outflow of fluids, vacuum packaging, and rehydration, while the support structure 360 can provide the desired support to limit damage to the tissue specimen G during storage, rehydration, and removal for use in a surgical procedure. The support structure 360 can be constructed of any suitable material, and has a third stiffness that is greater than both the first stiffness (of the first layer 310) and the second stiffness (of the second layer 320). In this manner, the support structure 360 functions as a rigid structure (relative to the flexible container 305) that can support the tissue specimen G during loading into the tissue container 305, storage within the tissue container 305, and subsequent rehydration and preparation for use in a surgical procedure. For example, in some embodiments, the third stiffness is at least two times greater than the first stiffness and the second stiffness. In other embodiments, the third stiffness is at least five times greater than the first stiffness and the second stiffness.

The higher stiffness of the support structure 360 can be related to any of the thickness of the support structure 360, the geometry (i.e., the cross-sectional geometry) of the support structure 360, and the material from which the support structure 360 is constructed. In some embodiments, the support structure 360 can be thicker than either the first layer 310 or the second layer 320. Specifically, in some embodiments, the support structure 360 can be at least twice as thick as either the first layer 310 or the second layer 320. In other embodiments, the support structure 360 can be at least three times as thick as either the first layer 310 or the second layer 320. Moreover, the support structure 360 can be constructed from any suitable polymer, such as, for example, a polyethylene terephthalate (PET) material, a polyethylene material, a polyvinyl chloride (PVC) material, a polyamide material, a polyester-based material, or any combination of such materials, including laminates constructed from multiple different materials. In some embodiments, the support structure 360 can be constructed from a different material than that from which the first layer 310 and/or the second layer 320 are constructed.

Figure 16:
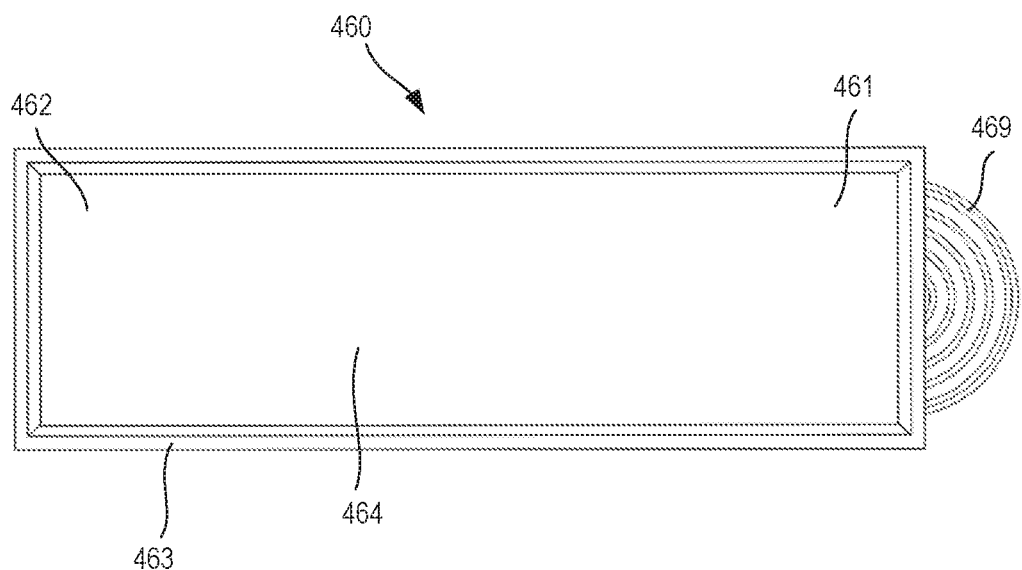
FIG. 16 is a top view and FIG. 17 is a side view of a support structure, according to an embodiment.
Figure 17:
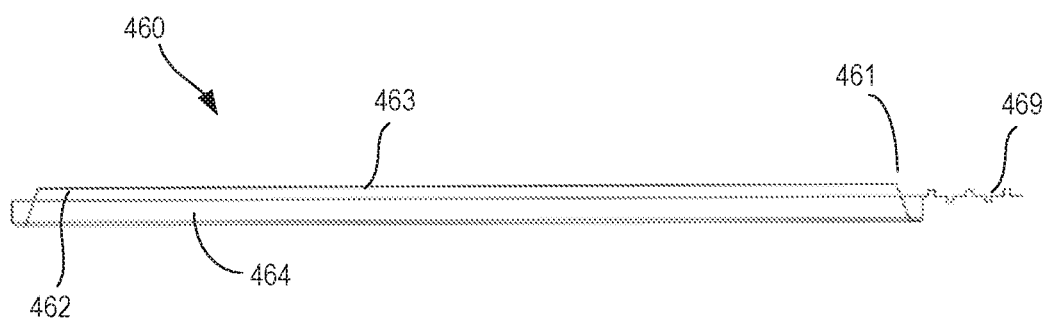

Although support structure 360 is shown as being a flat (or planar) structure, in other embodiments, the support structure 360 (and any of the support structures described herein) can be a tray-shaped structure that includes side edges. For example, in some embodiments, any of the container assemblies described herein can include the support structure 460 shown in FIGS. 16 and 17. The support structure 460 includes a first end portion 461, a second end portion 462, a bottom surface 464 and a raised side edge 463. The support structure 460 can be removably disposed within a flexible container, such as the flexible containers 205 and 305, and is configured to support a tissue specimen within the storage volume of the flexible container. In this manner, the support structure 460 can provide the desired support to limit damage to the tissue specimen (not shown in FIGS. 16 and 17) during storage, rehydration, and removal for use in a surgical procedure. Specifically, the tissue specimen can be placed on the bottom surface 464 and can be surrounded by raised side edge 463. The side edge 463 can reduce the likelihood that the tissue specimen will slide off the bottom surface 464 when the support member is being moved (e.g., to load the tissue container for storage or to remove the tissue specimen for use in a procedure). The side edge 463 also increases the cross-sectional area moment of inertia of the support structure 460 (as compared to that for a planar support structure), thereby increasing the stiffness of the support structure. Although the side edge 463 is shown as surrounding the entire perimeter of the bottom surface 464, in other embodiments a support structure can include an edge that only partially surrounds the bottom surface.

In addition to the side edge 463, the first end portion 461 of the support structure 460 also includes a tab 469. The tab 469 can be used to manipulate the support structure 460 during loading of the container, unloading of the container, or the like. In some embodiments, the tab 469 (or any other portion of the support structure 460) can include a label or indicium associated with the tissue specimen. In some embodiments, the label can be a machine-readable (and/or machine writable) label, such as a bar code, RFID, QR code, or the like. This arrangement can facilitate identification and tracking of the tissue specimen within the support structure 460 and/or the associated flexible container.

The support structure 460 can be constructed of any suitable material, and, in some embodiments, has a third stiffness that is greater than the stiffness of the flexible container within which the support structure is disposed. In this manner, the support structure 460 functions as a rigid structure (relative to the flexible container 405) that can support the tissue specimen during loading into the tissue container 405, storage within the tissue container 405, and subsequent rehydration and preparation for use in a surgical procedure. The support structure 460 can be constructed from any suitable polymer, such as, for example, a polyethylene terephthalate (PET) material, a polyethylene material, a polyvinyl chloride (PVC) material, a polyamide material, a polyester-based material, or any combination of such materials, including laminates constructed from multiple different materials. In some embodiments, the support structure 460 can be constructed from a different material than that from which the first layer 410 and/or the second layer 420 are constructed.

Figure 18:
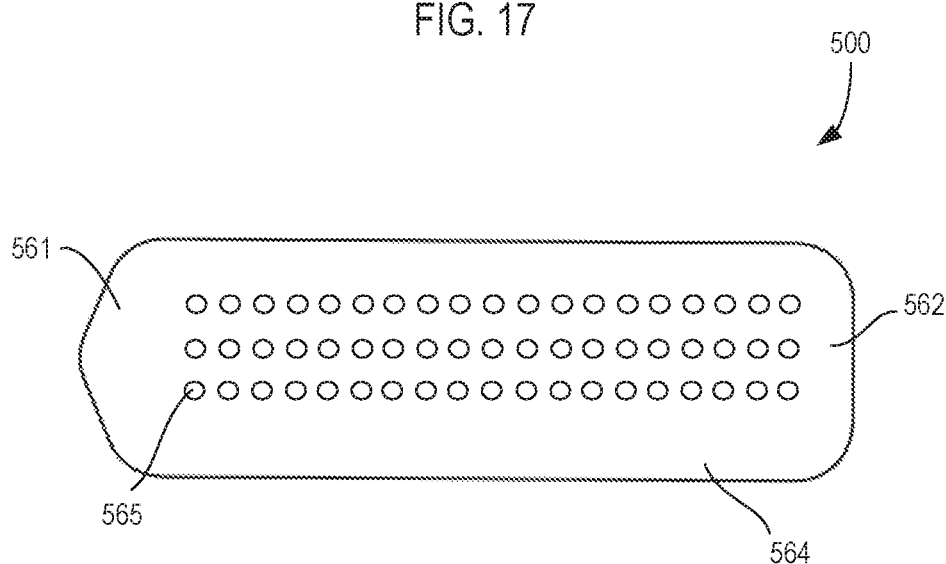
FIG. 18 is a top view of a support structure, according to an embodiment.

In some embodiments, any of the support structures disclosed herein can include one or more holes, channels, or grooves to facilitate rehydration. For example, in some embodiments, any of the support structures can define a series of through holes, like those shown in the support structure 560 shown in FIG. 18. The support structure 560 includes a first end 561, a second end 562, and a bottom surface 564. The support structure 560 can be removably disposed within a flexible container, such as the flexible containers 205 and 305, and is configured to support a tissue specimen within the storage volume of the flexible container. In this manner, the support structure 560 can provide the desired support to limit damage to the tissue specimen (not shown in FIG. 18) during storage, rehydration, and removal for use in a surgical procedure. As shown, the bottom surface 564 defines a series of holes 565 through which fluid can pass. In this manner, the side of the tissue specimen facing the bottom surface 564 can receive and/or be exposed to rehydration fluid when such fluid is conveyed into the flexible container (e.g., via any of the ports as described herein). In other embodiments, a support structure need not include holes or openings therethrough, but rather can include one or more channels or grooves through which the rehydration fluid can flow to reach the bottom side of the tissue specimen.

Although the container assembly 200 is shown and described as including a support structure that is removably disposed within the flexible container 205, in other embodiments, a container assembly can include a support structure that is fixedly coupled to the flexible container. Similarly stated, in some embodiments a container assembly can include a support structure that is captive with (or is non-removable from) the flexible container. In some embodiments, for example, the support structure (such as the support structure 260) can be bonded or attached to the one of the layers of the flexible container (e.g., the second layer 220). In other embodiments, a flexible container can define a captive pocket (or volume) within which the support structure is sealed. For example, FIGS. 19-22 show various views of a container assembly 600 according to an embodiment that includes a three-layer design with a captive support structure 660. The container assembly 600 (and any of the container assemblies described herein) can be used to perform any of the methods described herein, such as the method 10 of preparing a tissue specimen for storage (see FIG. 5) and/or the method 20 of rehydrating a tissue specimen for use in a procedure according to an embodiment (see FIG. 6). As described herein, the container assembly 600 provides a single container that can be used for both storage and rehydration. The container provides sufficient support for the tissue specimen or graft G, which can be very fragile during and after rehydration. As shown, the container assembly 600 includes a flexible container 605, a port 650 coupled to the flexible container 605, and a support structure 660.

The flexible container 605 includes a first end portion 601, a second end portion 602, and a pair of side edges 603 between the first end portion 601 and the second end portion 602. The flexible container 605 is constructed from a first layer 610, a second layer 620, and a third layer 630. The first layer 610 and the second layer 620 are coupled together to define a storage volume 606 within which the tissue specimen G can be contained. As shown in the side view of FIG. 19 when the container assembly 600 is in the first (or opened) configuration, an edge 611 of the first layer 610 is spaced apart from an edge 621 of the second layer 620 to define an opening 607 into the storage volume 606. The opening 607 can be of any suitable size to facilitate loading of the support structure 660 and the tissue specimen G, as described herein.

The second layer 620 and the third layer 630 are coupled together to define a support volume 634 within which the support structure 660 is sealed. In this manner, the support structure 660 is captive within the flexible container 605, and can be maintained in the desired position relative to the storage volume 606 and/or the tissue specimen G. As shown in the side views of FIGS. 19 and 22, an edge 631 of the third layer 630 is sealed to (or joined with) the edge 621 of the second layer 620 to enclose the support volume 634. The third layer 630 and the second layer 620 can be joined together at the first end portion 601 by any suitable mechanism, such as, for example, by heat bonding or by an adhesive. Although the edge 621 is shown as being between the edge 611 and the edge 631, in other embodiments, the third layer 630 can be sealed to the second layer 620 at any suitable location to enclose the support volume.

The first layer 610 can be constructed of any suitable material, and has a first stiffness. For example, in some embodiments, the first layer 610 can be a thin, peelable film, such as, for example, a heat seal-coated (HSC) material, a polyethylene material, a polyvinyl chloride (PVC) material, a polyamide material, a polyester-based material, or any combination of such materials, including laminates constructed from multiple different materials. For example, in some embodiments, the first layer 610 is a laminate that includes a substrate, a barrier coating, and an adhesive. The substrate can be, for example, a peelable film of the types (and thicknesses) described herein. The barrier coating can be any suitable coating, such as an aluminum oxide barrier coating of any suitable thickness (36 gauge, 40 gauge, 48 gauge, or any thickness therebetween). The adhesive can be any suitable adhesive that facilitates bonding of the first layer 610 to the second layer 620. Moreover, the first layer 610 can have any suitable thickness to provide the desired strength, flexibility, and sealing characteristics. For example, in some embodiments, the first layer 610 can be between about 50 microns (0.050 mm) and about 200 microns (0.200 mm). In other embodiments, the first layer can be between about 50 microns (0.050 mm) and about 100 microns (0.100 mm).

The second layer 620 can be constructed of any suitable material, and has a second stiffness. Likewise, the third layer 630 can be constructed of any suitable material, and has a third stiffness. For example, in some embodiments, the second layer 620 and/or the third layer 630 can constructed from the same material and/or can have the same stiffness as the first layer 610. In other embodiments, the second layer 620 and/or the third layer 630 can be constructed from a different material and the second stiffness and/or the third stiffness can be different than the first stiffness. The second layer 620 and/or the third layer 630 can be constructed from any suitable polymer, such as, for example, a heat seal-coated (HSC) material, a polyethylene material, a polyvinyl chloride (PVC) material, a polyamide material, a polyester-based material, or any combination of such materials, including laminates constructed from multiple different materials. For example, in some embodiments, the second layer 620 and/or the third layer 630 is a laminate that includes a substrate, a barrier coating, and an adhesive. The substrate can be constructed from any of the materials described herein. The barrier coating can be any suitable coating, such as an aluminum oxide barrier coating of any suitable thickness (36 gauge, 40 gauge, 48 gauge, or any thickness therebetween). The adhesive can be any suitable adhesive that facilitates bonding of the first layer 610 to the second layer 620. Moreover, the second layer 620 and/or the third layer 630 can have any suitable thickness to provide the desired strength, flexibility, and sealing characteristics. For example, in some embodiments, the second layer 620 can be between about 50 microns (0.050 mm) and about 200 microns (0.200 mm). In other embodiments, the second layer 620 can be between about 50 microns (0.050 mm) and about 100 microns (0.100 mm).

The materials from which the first layer 610, the second layer 620, and the third layer 630 are constructed are selected to ensure that the three layers can be joined to hermetically seal the storage volume 606 within which the tissue graft G is stored (and the support volume 634 within which the support structure 660 is contained) while also retaining the desired flexibility. Specifically, as shown, the two three layers are joined at the first end portion 601 and at the second end portion 602 with the port 650 therebetween. As shown in FIG. 22, the edge 611 of the first layer 610 and the edge 621 of the second layer 620 are configured to be joined together after the tissue graft G is loaded into the storage volume 606 to form a peelable seal 614 that hermetically seals the storage volume 606. The peelable seal 614 can be configured to have any suitable failure (or peel) mechanism as described herein, and can be of any suitable peel strength. The peelable seal 614 can be produced by any suitable mechanism as described herein, such as, for example, by a heat sealing operation.

As described above, the port 650 is coupled to the second end portion 602 of the container assembly 600 and is configured to allow fluid communication between a volume outside of the container assembly 600 and the storage volume 606. Thus, the port 650 can be used to provide access to the storage volume 606 and the tissue specimen G after the first end portion 601 has been sealed closed. In this manner, the tissue specimen G can be treated with a preservation fluid or other material after being sealed into the container assembly 600. The port 650 can also be coupled to a vacuum source to evacuate the storage volume for storage of the tissue specimen G. Moreover, during a surgical procedure, the port 650 can allow for inflow of rehydration fluid. The port 650 can be any suitable port that selectively provides fluid communication to the storage volume 606, such as the port 250 described above. The port 650 can include a tube 651, a valve, and/or a cap 653.

The support structure 660 is configured to support the tissue specimen within the storage volume 606. In this manner, the flexible container 605 can be sufficiently flexible to allow inflow and outflow of fluids, vacuum packaging, and rehydration, while the support structure 660 can provide the desired support to limit damage to the tissue specimen G during storage, rehydration, and removal for use in a surgical procedure. The support structure 660 can be constructed of any suitable material, and has a stiffness that is greater than the first stiffness (of the first layer 610), the second stiffness (of the second layer 620), and the third stiffness (of the third layer 630). In this manner, the support structure 660 functions as a rigid structure (relative to the flexible container 605) that can support the tissue specimen G during loading into the tissue container 605, storage within the tissue container 605, and subsequent rehydration and preparation for use in a surgical procedure.

The higher stiffness of the support structure 660 can be related to any of the thickness of the support structure 660, the geometry (i.e., the cross-sectional geometry) of the support structure 660, and the material from which the support structure 660 is constructed. In some embodiments, the support structure 660 can be thicker than the first layer 610, the second layer 620, or the third layer 630. Specifically, in some embodiments, the support structure 660 can be at least twice as thick as either the first layer 610, the second layer 620, or the third layer 630. In other embodiments, the support structure 660 can be at least three times as thick as either the first layer 610, the second layer 620, or the third layer 630. Moreover, the support structure 660 can be constructed from any suitable polymer, such as, for example, a polyethylene terephthalate (PET) material, a polyethylene material, a polyvinyl chloride (PVC) material, a polyamide material, a polyester-based material, or any combination of such materials, including laminates constructed from multiple different materials. In some embodiments, the support structure 660 can be constructed from a different material than that from which the first layer 610, the second layer 620 and/or the third layer 630 are constructed.

Figure 23:
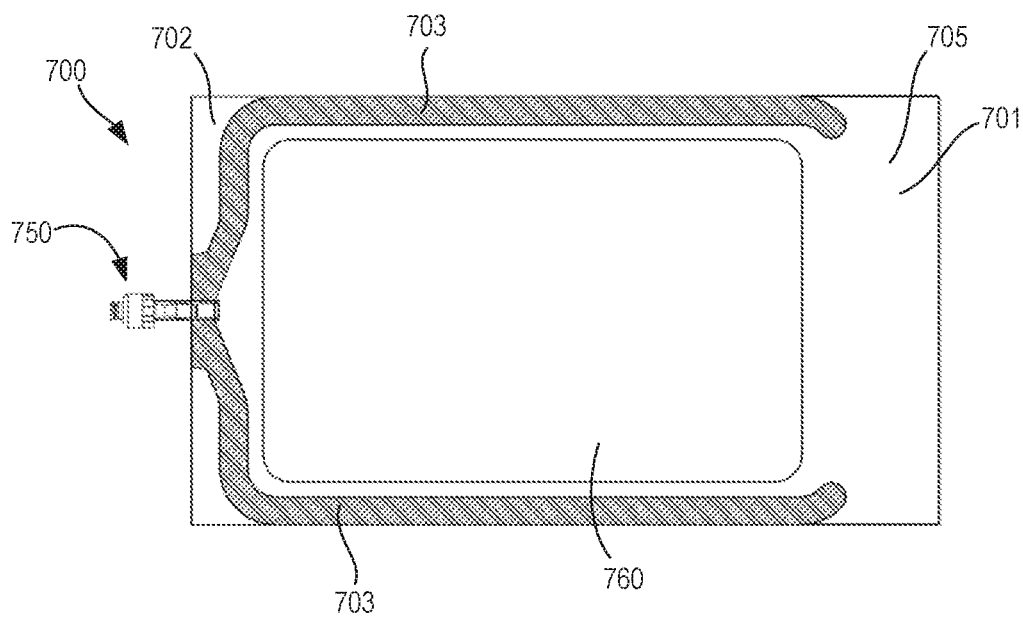
FIG. 23 is a top view of a container assembly in an opened configuration, according to an embodiment.
Figure 24:
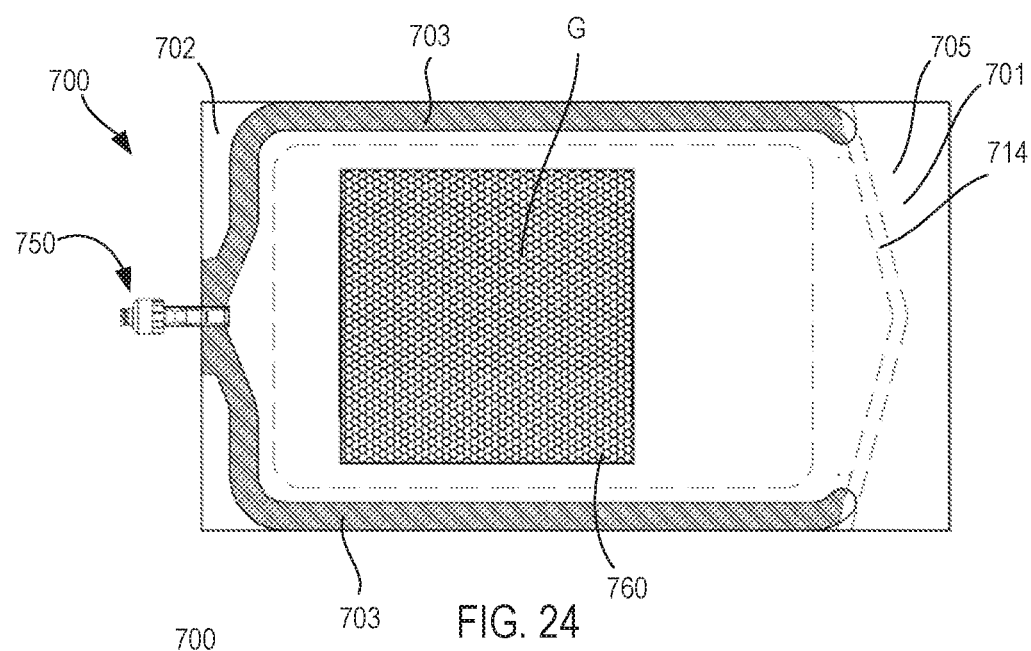
FIG. 24 is a top view and FIG. 25 is a side view of the container assembly shown in FIG. 23 in a sealed configuration with a tissue specimen contained therein.
Figure 25:
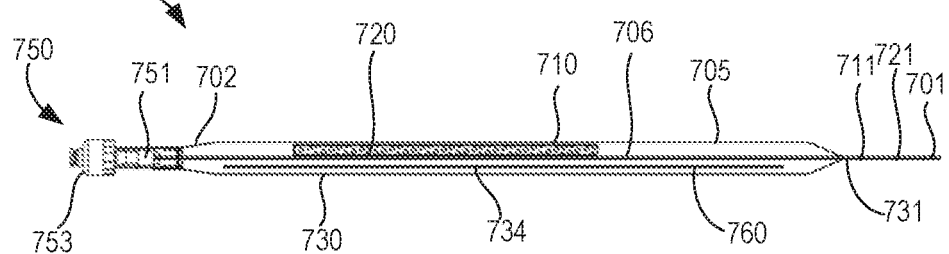

FIGS. 23-25 show various views of a container assembly 700 according to an embodiment that includes another three-layer design with a captive support structure 760, according to an embodiment. The container assembly 700 (and any of the container assemblies described herein) can be used to perform any of the methods described herein, such as the method 10 of preparing a tissue specimen for storage (see FIG. 5) and/or the method 20 of rehydrating a tissue specimen for use in a procedure according to an embodiment (see FIG. 6). As described herein, the container assembly 700 provides a single container that can be used for both storage and rehydration. The container provides sufficient support for the tissue specimen or graft G, which can be very fragile during and after rehydration. The container assembly 700 is similar in many respects to the container assembly 600, and includes a flexible container 705, a port 750 coupled to the flexible container 705, and a support structure 760.

The flexible container 705 includes a first end portion 701, a second end portion 702, and a pair of side edges 703 between the first end portion 701 and the second end portion 702. The flexible container 705 is constructed from a first layer 710, a second layer 720, and a third layer 730. The first layer 710 and the second layer 720 are coupled together to define a storage volume 706 within which the tissue specimen G can be contained. When the container assembly 700 is in the first (or opened) configuration, an edge 711 of the first layer 710 is spaced apart from an edge 721 of the second layer 720 to define an opening (not shown) into the storage volume 706.

The second layer 720 and the third layer 730 are coupled together to define a support volume 734 within which the support structure 760 is sealed. In this manner, the support structure 760 is captive within the flexible container 705, and can be maintained in the desired position relative to the storage volume 706 and/or the tissue specimen G. An edge 731 of the third layer 730 is sealed to (or joined with) the edge 721 of the second layer 720 to enclose the support volume 734. The third layer 730 and the second layer 720 can be joined together at the first end portion 701 by any suitable mechanism, such as, for example, by heat bonding or by an adhesive.

The first layer 710 can be constructed of any suitable material, and has a first stiffness, in a similar manner as that described above for the first layer 610. The second layer 720 can be constructed of any suitable material, and has a second stiffness, in a similar manner as that described above for the second layer 620. Likewise, the third layer 730 can be constructed of any suitable material, and has a third stiffness, in a similar manner as that described above for the third layer 630. As shown in FIG. 25, the edge 711 of the first layer 710 and the edge 721 of the second layer 720 are configured to be joined together after the tissue graft G is loaded into the storage volume 706 to form a peelable seal 714 that hermetically seals the storage volume 706. The peelable seal 714 can be configured to have any suitable failure (or peel) mechanism as described herein, and can be of any suitable peel strength. The peelable seal 714 can be produced by any suitable mechanism as described herein, such as, for example, by a heat sealing operation.

As described above, the port 750 is coupled to the second end portion 702 of the container assembly 700 and is configured to allow fluid communication between a volume outside of the container assembly 700 and the storage volume 706. Thus, the port 750 can be used to provide access to the storage volume 706 and the tissue specimen G after the first end portion 701 has been sealed closed. The port 750 can be any suitable port that selectively provides fluid communication to the storage volume 706, such as the port 250 described above. The port 750 can include a tube 751, a valve, and/or a cap 753.

The support structure 760 is configured to support the tissue specimen within the storage volume 706. In this manner, the flexible container 705 can be sufficiently flexible to allow inflow and outflow of fluids, vacuum packaging, and rehydration, while the support structure 760 can provide the desired support to limit damage to the tissue specimen G during storage, rehydration, and removal for use in a surgical procedure. The support structure 760 can be constructed of any suitable material, as that described above for the support structure 660.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

Although various embodiments have been described as having particular features and/or combinations of components, other embodiments are possible having a combination of any features and/or components from any of embodiments as discussed above. Aspects have been described in the general context of medical devices, and more specifically tissue packaging devices, but inventive aspects are not necessarily limited to use in medical devices and tissue packaging.

What is claimed is:

1. An apparatus, comprising:
a flexible container including a first layer coupled to a second layer to define a storage volume within which a tissue specimen can be contained, the first layer characterized by a first stiffness, the second layer characterized by a second stiffness, an edge of the first layer spaced apart from an edge of the second layer to define an opening into the storage volume, the edge of the first layer and the edge of the second layer configured to form a peelable seal that hermetically seals the storage volume such that the first layer can be peeled away from the second layer to expose the storage volume;
a port coupled to the flexible container, the port configured to allow fluid communication between the storage volume and an external volume; and
a support structure configured to support the tissue specimen within the storage volume, the support structure characterized by a third stiffness, the third stiffness greater than the first stiffness and the second stiffness.

2. The apparatus of claim 1, wherein:
the edge of the first layer and the edge of the second layer are at a first end of the flexible container; and
the port is coupled at a second end of the flexible container, the second end opposite the first end.

3. The apparatus of claim 1, wherein:
the port is coupled at an end of the flexible container, a center line of the port being aligned with a longitudinal axis of the flexible container; and
the edge of the first layer and the edge of the second layer are at a side of the flexible container extending along the longitudinal axis.

4. The apparatus of claim 1, wherein:
the first layer is a first laminate including a first substrate, a first barrier coating, and a first adhesive, the first substrate being a peelable film; and
the second layer is a second laminate including a second substrate, a second barrier coating, and a second adhesive, the second substrate being a different material than the first substrate.

5. The apparatus of claim 4, wherein at least one of the first barrier coating or the second barrier coating includes aluminum oxide.

6. The apparatus of claim 1, wherein a thickness of the support structure is at least two times greater than each of a thickness of the first layer and a thickness of the second layer.

7. The apparatus of claim 4, wherein the support structure is constructed from a different material than the first substrate or the second substrate.

8. The apparatus of claim 7, wherein:
the second substrate is constructed from linear low-density polyethylene (LLDPE); and
the support structure is constructed from polyethylene terephthalate glycol.

9. The apparatus of claim 1, wherein the support structure is configured to be disposed within the storage volume and defines a series of hydration openings.

10. The apparatus of claim 1, wherein the port includes a needle-free valve configured to selectively allow fluid communication between the storage volume and the external volume.

11. An apparatus, comprising:
a flexible container including a first layer, a second layer, and a third layer, the first layer coupled to the second layer to define a storage volume within which a tissue specimen can be contained, the third layer coupled to the second layer to define a support volume, an edge of the first layer spaced apart from an edge of the second layer to define an opening into the storage volume, the edge of the first layer and the edge of the second layer configured to form a peelable seal that hermetically seals the storage volume such that the first layer can be peeled away from the second layer to expose the storage volume;
a port coupled to the flexible container, the port configured to allow fluid communication between the storage volume and an external volume; and
a support structure within the support volume, the support structure configured to support the tissue specimen within the storage volume.

12. The apparatus of claim 11, wherein an edge of the third layer is sealed to the edge of the second layer to seal the support structure within the support volume.

13. The apparatus of claim 11, wherein:
the first layer is a first laminate including a first substrate, a first barrier coating, and a first adhesive, the first substrate being a peelable film;
the second layer is a second laminate including a second substrate, a second barrier coating, and a second adhesive, the second substrate being a different material than the first substrate; and
the support structure is constructed from a different material than the first substrate or the second substrate.

14. A method, comprising:
inserting a tissue specimen into a storage volume defined between a first layer of a flexible container and a second layer of the flexible container, the tissue specimen inserted via an opening defined by an edge of the first layer and an edge of the second layer, the flexible container including a port configured to allow fluid communication between the storage volume and an external volume;
positioning the tissue specimen within the storage volume between the first layer and a support structure, a stiffness of the support structure greater than each of a stiffness of the first layer and a stiffness of the second layer; and
coupling the edge of the first layer to the edge of the second layer to form a peelable seal that hermetically seals the storage volume, the peelable seal configured such that the first layer can be peeled away from the second layer to expose the storage volume.

15. The method of claim 14, further comprising:
placing, before the inserting, the tissue specimen on the support structure, the inserting includes inserting the tissue specimen and the support structure into the storage volume.

16. The method of claim 14, wherein:
the flexible container includes a third layer coupled to the second layer to define a support volume; and
the support structure is within the support volume.

17. The method of claim 16, wherein an edge of the third layer is sealed to the edge of the second layer to seal the support structure within the support volume.

18. The method of claim 17, wherein the edge of the second layer is between the edge of the first layer and the edge of the third layer.

19. The method of claim 14, wherein the coupling includes:
placing the edge of the first layer and the edge of the second layer in a band sealer;
heating the edge of the first layer and the edge of the second layer to a sealing temperature of between about 125C and 135C;
applying a sealing pressure of between 480 kPA and 520 kPa to the edge of the first layer and the edge of the second layer; and
maintaining the sealing temperature for about 3 seconds.

20. The method of claim 14, further comprising:
conveying, after the coupling, a preservation fluid into the storage volume via the port.

\* \* \* \* \*